US011547818B2

(12) United States Patent
Othel-Jacobsen et al.

(10) Patent No.: US 11,547,818 B2
(45) Date of Patent: Jan. 10, 2023

(54) BREATHING DEVICE

(71) Applicant: Rehaler ApS, Aarhus C (DK)

(72) Inventors: Erik Othel-Jacobsen, Hellerup (DK);
Asger Johansen, Copenhagen S (DK);
Troels Johansen, Aarhus C (DK)

(73) Assignee: Rehaler ApS, Aarhus C (DK)

( * ) Notice: Subject to any disclaimer, the term of this patent is extended or adjusted under 35 U.S.C. 154(b) by 869 days.

(21) Appl. No.: 15/998,585

(22) PCT Filed: Feb. 16, 2017

(86) PCT No.: PCT/DK2017/050043
§ 371 (c)(1),
(2) Date: Aug. 16, 2018

(87) PCT Pub. No.: WO2017/140322
PCT Pub. Date: Aug. 24, 2017

(65) Prior Publication Data
US 2019/0351161 A1   Nov. 21, 2019

(30) Foreign Application Priority Data

Feb. 16, 2016 (DK) .......................... PA 2016 70086
Nov. 11, 2016 (DK) .......................... PA 2016 70900

(51) Int. Cl.
*A61M 16/00* (2006.01)
*A61M 16/06* (2006.01)
*A61M 16/20* (2006.01)

(52) U.S. Cl.
CPC .... *A61M 16/0045* (2013.01); *A61M 16/0078* (2013.01); *A61M 16/06* (2013.01); *A61M 16/20* (2013.01); *A61M 2202/0225* (2013.01); *A61M 2230/432* (2013.01)

(58) Field of Classification Search
CPC .......... A61M 16/0078; A61M 16/0045; A61M 2230/432; A61M 16/20
See application file for complete search history.

(56) References Cited

U.S. PATENT DOCUMENTS 2,634,724 A * 4/1953 Henryl ............... A41D 13/1123
128/206.19
2,652,830 A 9/1953 Koza et al.
(Continued)

FOREIGN PATENT DOCUMENTS

DE 19912337 C1 * 8/2000 ........ A61M 16/0045
DE 19912337 C1 8/2000
(Continued)

OTHER PUBLICATIONS

Bruecken at al., English Translation of DE19912337C1, http://espacenet.com (Year: 2021).*
(Continued)

*Primary Examiner* — Margaret M Luarca
*Assistant Examiner* — Cana A Gallegos
(74) *Attorney, Agent, or Firm* — Taft Stettinius & Hollister LLP

(57) ABSTRACT

A breathing device, comprising a mouthpiece forming a breathing channel, to form a connection between a first end and a second end of the mouthpiece; the first end being configured for a user breathing into the mouthpiece through a breathing opening; an at least partly flexible rebreathing air chamber attached to the second end of the mouthpiece, thereby being in fluid connection with the breathing channel; the rebreathing air chamber being formed by at least partly flexible wall section(s), the at least partly flexible rebreathing chamber having at a first wall section, being permeable
(Continued)

to gas by a plurality of pores provided in said wall section and/or the mouth piece comprising one or more though going openings.

21 Claims, 18 Drawing Sheets

(56) References Cited

U.S. PATENT DOCUMENTS

| | | | |
|---|---|---|---|
| 3,097,642 A | | 7/1963 | Russell |
| 4,098,271 A | | 7/1978 | Maddock |
| 4,192,301 A | | 3/1980 | Hardwick |
| 4,275,722 A | | 6/1981 | Sorensen |
| 4,301,810 A | | 11/1981 | Belman |
| 4,327,741 A | | 5/1982 | Watson et al. |
| 4,508,116 A | | 4/1985 | Duncan et al. |
| 4,628,926 A | * | 12/1986 | Duncan ............ A61M 16/0045 128/203.28 |
| 4,919,132 A | * | 4/1990 | Miser .................. A61M 16/00 116/277 |
| 2006/0130839 A1 | * | 6/2006 | Bassovitch ....... A61M 16/0045 128/205.28 |
| 2009/0241959 A1 | | 10/2009 | Halpern |
| 2012/0240935 A1 | | 9/2012 | Johansen |
| 2013/0172762 A1 | | 7/2013 | Stabler et al. |
| 2013/0172768 A1 | | 7/2013 | Lehman |
| 2014/0090644 A1 | * | 4/2014 | Aldana ................ A61M 16/12 128/203.23 |
| 2016/0095994 A1 | * | 4/2016 | Currin ................ A61M 16/026 128/203.14 |

FOREIGN PATENT DOCUMENTS

| | | |
|---|---|---|
| EP | 2338575 A1 | 6/2011 |
| EP | 2488242 B1 | 9/2019 |
| GB | 571555 A | 8/1945 |
| GB | 2113555 A | 8/1983 |
| GB | 2378094 A | 1/2003 |
| WO | 9728837 A1 | 8/1997 |

OTHER PUBLICATIONS

International Search Report; European Patent Office; International Application No. PCT/DK2017/050043; dated May 8, 2017; 4 pages.
Written Opinion of the International Searching Authority; European Patent Office; International Application No. PCT/DK2017/050043; dated May 8, 2017; 7 pages.
International Preliminary Report on Patentability; The International Bureau of WIPO; International Application No. PCT/DK2017/050043; dated Aug. 21, 2018; 8 pages.

* cited by examiner

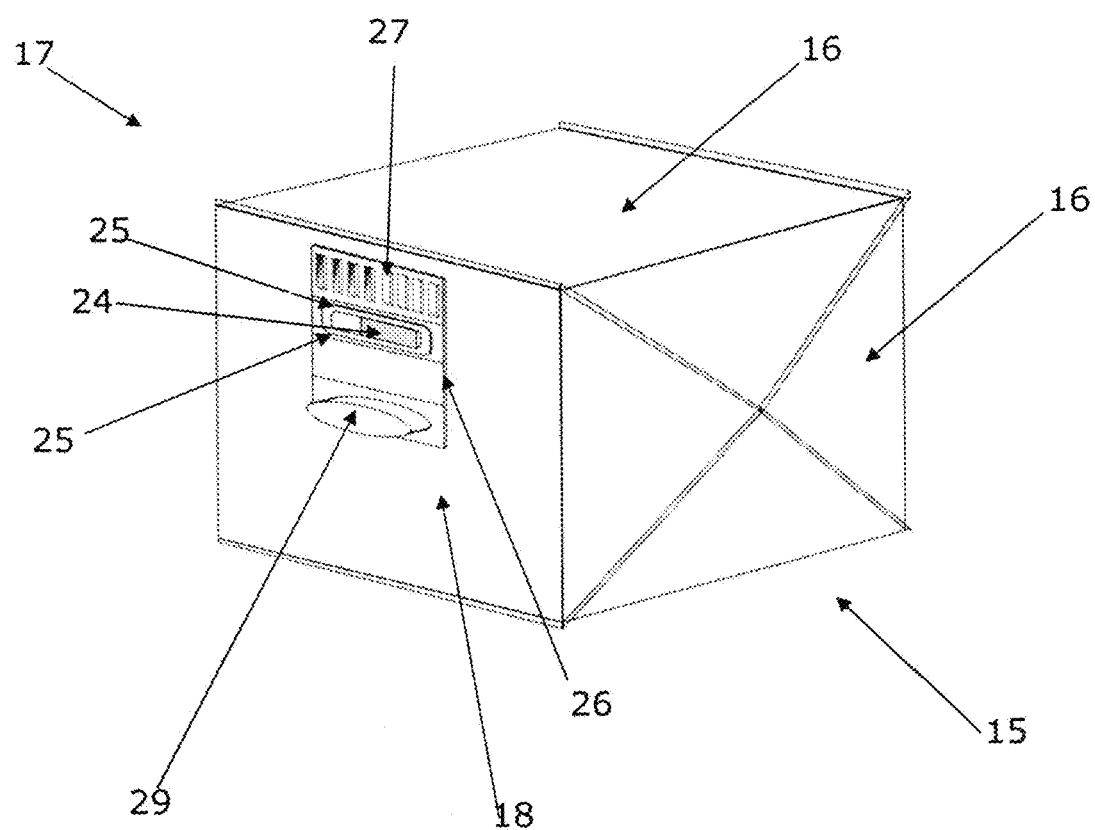
Figure 11.a

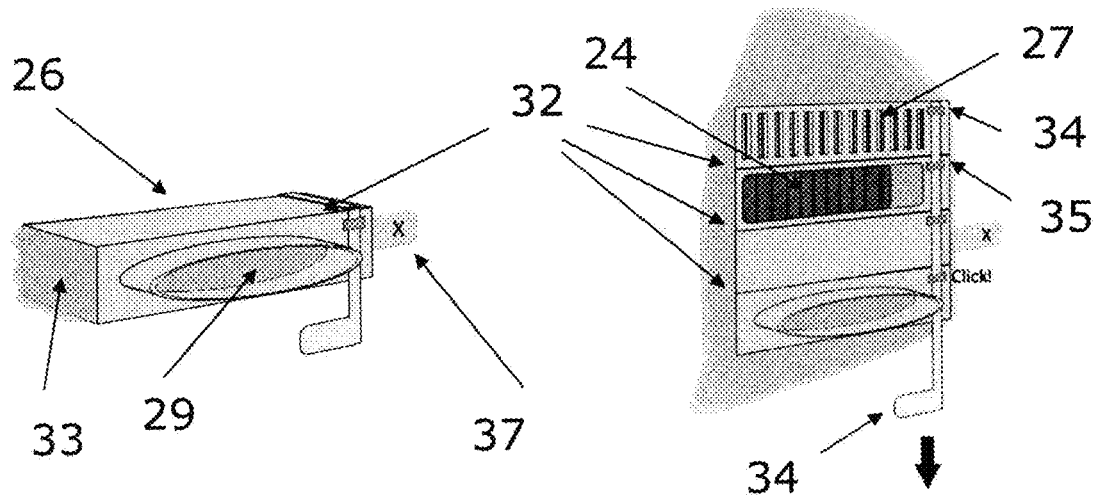
Fig. 16a
Fig. 16b
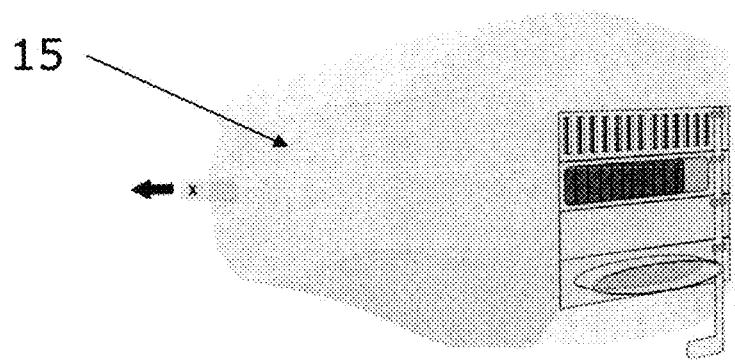
Fig. 16c

BREATHING DEVICE

CROSS-REFERENCE TO RELATED APPLICATIONS

This application is a U.S. National Phase of International PCT Application No. PCT/2017/050043 filed Feb. 16, 2017, which claims priority to Danish Patent Application No. PA 2016 70086 filed Feb. 16, 2016 and Danish Patent Application No. PA 2016 70900 filed Nov. 11, 2016, each of which are incorporated herein by reference in their entirety.

FIELD OF THE INVENTION

The present invention relates to a breathing device for increasing the level of $CO_2$ in the inhaled air. Several breathing devices for increasing the level of $CO_2$ in inhaled air are known. Such devices may be a simple mask covering the user's mouth and nose or a mask connected to a bag, which is able to expand and retract during breathing. The mask may be equipped with a valve or similar which allows fresh air into the mask.

BACKGROUND OF THE INVENTION

In a range of different common medical disorders (among them migraine, epilepsy, post-spinal headache, febrile seizures, idiopathic dyspnoea, the hyperventilation syndrome, panic anxiety, asthma, and certain heart conditions) it has been demonstrated that a positive treatment effect can be obtained by raising the $CO_2$ concentration in the patient's inspired air. In the body, raising $CO_2$ concentration will, among other effects, lower the pH value of the bodily fluids, increase the cerebral blood flow and lower the excitability of the nervous system.

OBJECT OF THE INVENTION

An object of the present invention is to provide an improvement of breathing devices for increasing the level of $CO_2$ in the inhaled air.

Another object of the present invention is to provide a device which may relieve the symptoms of migraine, post-spinal headache or other types of headache, or optionally inhibit and/or prevent an attack of migraine in a user suffering from migraine.

A further object is to provide a device which may be used for relieving or preventing epileptic attacks and/or febrile seizures.

A further object is to provide a device which may be used for the preventive treatment of asthma.

A further object is to provide a device which may be used for improving rehabilitation after cardiac arrest.

A further object is to provide a device which may serve to increase the cerebral blood flow and oxygen delivery to the brain by the vasodilatory action of $CO_2$.

A further object is to provide a device which during use may decrease the excitability of the nervous system by inducing acidosis in a user, mediated by increasing the inspired partial pressure of $CO_2$.

SUMMARY OF THE INVENTION

The invention relates to a breathing device, comprising a mouthpiece forming a breathing channel to form a connection between a first end and a second end of the mouthpiece, the first end being configured for a user breathing into the mouthpiece through a breathing opening, an at least partly flexible rebreathing air chamber attached to the second end of the mouthpiece, thereby being in fluid connection with the breathing channel, the rebreathing air chamber being formed by at least partly flexible wall section(s) having at a first wall section being permeable to gas by a plurality of pores provided in said wall section.

Preferably, the at least partly flexible rebreathing chamber has a first wall section being permeable to gas by one or more, such as a plurality of pores and/or through going openings provided in said wall section and/or preferably, the mouth piece may comprise one or more though going openings allowing fluid communication between the breathing channel and the surrounding atmosphere.

The invention also relates to a breathing device for increasing the level of $CO_2$ in the inhaled air.

The wall of the rebreathing air chamber may further comprise a wall section with a number of through-going openings and/or pores which provide a permeability to gas and which in combination have an overall flow conductance G. The wall section material in itself may be non-permeable to gas and deformable by a pressure differences across it, giving the wall section a substantial time-normalized compliance C, where C is determined as the volume expansion of the rebreathing chamber per second per pressure difference across the wall section.

The breathing device may also comprise a rebreathing air chamber, being formed by at least partly flexible wall section(s) being permeable to gas by a plurality of pores provided in the wall section(s).

The breathing device may also be formed by a flexible wall section, being permeable to gas by a plurality of pores arranged in lines or rows, distributed in the flexible wall section.

The form of the rebreathing air chamber is preferably selected from the group comprising: cube, such as cuboid, sphere, such as spheroid, bag type, tetrahedron, such as substantially tetrahedron, square-based pyramid such as substantially pyramid, octahedron, such as substantially octahedron, hexagonal prism such as substantially prism, dodecahedron, such as substantially dodecahedron, cylinder, or cylindroid.

Please observe, that due to the flexibility of the rebreathing air chamber, the shape thereof varies slightly due to the pressure difference between inside and outside, whereby for instance a cube can be deformed into a cuboid where the edges of the cube to some extend vanish due to a rounding of the panel.

In another embodiment of the present invention, the rebreathing air chamber may be in the form of a cuboid, such as a cube, comprising six wall sections each defining a face of the cube. Five of the six wall sections is preferably formed by a first flexible wall section type, and one of the six wall section by a second flexible wall section type. The second flexible wall section type may be impermeable to gas, and the first wall section type may comprise permeable sections or being permeable to gas by a plurality of pores preferably arranged in lines or rows, distributed in the flexible first wall section type.

The first wall section and second wall section may be impermeable to gas.

The permeable sections of the flexible first wall section type may have a thickness smaller than $10^{-2}$ m, such as smaller than $10^{-3}$ m, preferably equal to or less than $20*10^{-6}$ m The flexible first wall section type may further comprise impermeable sections having a thickness smaller than $10^{-2}$ m, such as smaller than $10^{-3}$ m, preferably equal to or less than $40*10^{-6}$ m.

The impermeable second flexible wall section type may have a thickness smaller than $10^{-2}$ m, such as smaller than $10^{-3}$ m, preferably equal to or less than $40*10^{-6}$ m.

In another embodiment of the present invention, the rebreathing air chamber may further comprise a breathing channel arranged on/in the flexible wall section, allowing fluid communication in and/or out of the rebreathing air chamber with the user's mouth, during use.

The breathing channel may have at least one through going opening, allowing fluid communication in and/or out of the breathing device with the surrounding atmosphere.

Preferably, one or more of the through going openings are re-closable and/or adjustable.

The through going openings may be in the form of an opening, provided by a slider arranged between two parallel longitudinal wall sections. The slider provides an opening into the breathing channel when the slider is moved to one side between the two parallel longitudinal wall sections. The slider is preferably configured for adjusting the flow of air into said rebreathing air chamber.

The breathing channel may further comprise two parallel longitudinal wall sections, protruding in a perpendicular direction to a breathing direction through the breathing channel, with a distance in between below 3 cm, such as below 2 cm preferably below 1 cm. The two parallel longitudinal wall sections may be configured preventing the user from blocking the through going openings with a finger, while holding the breathing device with the fingers. The through going openings is preferably arranged in between the two parallel longitudinal wall sections.

In another embodiment of the present invention, the breathing air chamber may further comprise one or more re-closable and/or adjustable openings, preferably a slider arranged between two parallel longitudinal wall sections. The slider is preferably arranged on the flexible wall section, providing an opening into the breathing air chamber when the slider is moved to one side between the two parallel longitudinal wall sections. The slider may be configured for adjusting the flow of air from the surrounding atmosphere into the rebreathing air chamber.

The flexible wall sections are preferably foldable such as by being pleated.

The rebreathing air chamber may be assembled by a plurality of wall elements, welded together to form a cube.

The rebreathing air chamber may also be assembled by four wall elements welded together to form a cube, each of the four wall element being formed by two triangular wall elements arranged on opposite to each other sides of one square wall element.

The plurality of pores may be equidistantly disturbed in the flexible wall sections(s).

Preferably, the hydraulic diameter of said pores is smaller than $10^{-2}$ m, such as smaller than $10^{-3}$ m, preferably equal to or smaller than $180*10^{-6}$ m. In other embodiments, the hydraulic diameter is selected between $100*10^{-6}$ m to 2 cm, such as $100*10$ cm$^{-6}$ m to 3 cm per through going opening.

The breathing opening may comprise a connection, such as a pipe, duct or other connection, suitable for connecting the breathing device to a facial mask.

The first wall and/or second wall section is preferably wholly or partially hydrophobic.

The rebreathing air chamber may have a volume between 1 and 16 liters, such as between 2 liter and 8 liter, preferably between 4 liter and 6 liter.

The first wall section and/or the second wall section may be foldable such as pleated.

The rebreathing air chamber may be sizeable by changing the geometry of the first wall section.

The breathing channel preferably has a cross-section of at least 1.0 cm$^2$, such at least 1.5 cm$^2$, preferably at least 2.0 cm$^2$. The breathing channel may be formed by a plurality of channels.

Preferably, the first wall section has an average pore size between about 2 nanometers and 2 millimetres.

The pores are preferably made by laser perforation.

The permeable and/or porous material may have a gas permeation flux for standard air determined at 20° C. and standard atmosphere (101.325 kPa), wherein the gas permeation flux preferably is at least about 0.0005 m3/(sec*m2*kPa) at a pressure difference as disclosed herein.

The permeable material comprises a polymer membrane, preferably comprising polytetrafluoroethylene (PTFE), perfluoroalkoxy (PFA), fluorinated ethylene propylene (FEP), polyvinylidene difluoride (PVDF), polyethylene (PE), polypropylene (PP), paper, vegetable fibres and/or combinations comprising any of the above-mentioned polymers.

Preferably, at least a part of the rebreathing air chamber is non-collapsible, preferably at least a part of rebreathing air chamber is non-collapsible and a part of the rebreathing air chamber is collapsible. More preferably, the rebreathing air chamber is partly collapsible and at least a sub-compartment closer to the breathing opening into the rebreathing air chamber is not collapsible or at least less collapsible than a sub-compartment farther from the breathing opening.

The breathing device may comprise at least one through going opening, allowing fluid communication in and/or out of the breathing device with the surrounding atmosphere, preferably provided in the mouthpiece.

Preferably, one or more of the at least one through going opening is provided with a valve, preferably an adjustable valve for regulating the gas flow through the aperture. The adjustable valve may be manually and/or automatically adjusted.

The rebreathing air chamber may comprise a valve for draining off condensed water.

The breathing device may comprise a $CO_2$ or $O_2$ sensing device, configured to measure the $CO_2$ and/or $O_2$ level of the inhaled and/or expired air.

The breathing device may comprise at least one moisture-absorbing element, configured to absorb moisture from the rebreathing air chamber. The moisture absorbing element(s) is preferably being at least partly placed in the rebreathing air chamber. The moisture-absorbing element may be a removable and replaceable element.

The breathing device may comprise a flavouring device, such as flavouring to have the flavour of menthol, configured to change the odour of the rebreathing gas.

The first and/or the second wall section may comprise a water-transporting element, configured to drain off water from the rebreathing air chamber. The water-transporting element is preferably made from or comprises a material which provides a path for transporting water from the rebreathing air chamber to the surrounding atmosphere or to a water-collecting unit.

The breathing device may further comprise a cabinet inside which the mouthpiece and the rebreathing air chamber is stored when not in use.

The mouthpiece and the rebreathing air chamber is/are preferably and/or repositionable replaceable and/or repositionable arranged in/on the cabinet.

The cabinet preferably comprises two detachable cabinet elements, such as lids, each detachably attached to an end of the cabinet. The two detachable cabinet elements may prevent access to either the rebreathing air chamber or breathing channel when device is not in use. The detachable cabinet elements may be configured to provide access to the rebreathing air chamber and/or to the breathing channel when detached.

The cabinet elements are preferably configured for being attached on two sides adjacent to the ends where there is access to either the rebreathing air chamber or breathing channel during non-use, so as to provide a better grip on the breathing device in use.

Preferably, the rebreathing air chamber is detachable from, and re-attachable to, the mouth piece.

The breathing device may further comprise a stability chamber/structure attached (but preferably not in direct fluid connection) to the rebreathing air chamber, configured to prevent collapse of the rebreathing air chamber or mouthpiece during the inhalation phase of the rebreathing.

The breathing device may also comprise one or more deflation valves configured to empty the rebreathing air chamber of air.

The breathing device may be used in the treatment of migraine.

The breathing device may be used in the treatment of epilepsy

The breathing device may be used in the treatment of febrile seizures.

The breathing device may be used in the preventive treatment of asthma.

The breathing device may be used in the treatment/rehabilitation after cardiac arrest.

The breathing device may be used in the treatment of post-spinal headache.

The rebreathing air chamber is preferably foldable to reduce its size.

In a further aspects, the invention relates to a breathing device comprising a rebreathing air-chamber-connector as presented herein, a rebreathing air-chamber connector for connecting a rebreathing air-chamber to a mount piece as such, or a rebreathing air-chamber connector for a rebreathing air-chamber where the rebreathing air-chamber forms a mount piece. In such aspect, the rebreathing air-chamber-connecter is foldable preferably by comprising a number of preferably parallel extending folding lines arranged in said connector to allow the air-breathing connector to be folded into a configuration defining a void, preferably being cuboid. The dimension of the breathing air-chamber connector preferably being selected so that when in folded configuration, at least part, preferably most of, such as all of the rebreathing air-chamber is accommodated inside the void. It is noted that the rebreathing air-chamber is folded when accommodated inside the void.

Preferably, such rebreathing air-chamber-connectors may preferably comprise a slider providing an opening into said breathing air chamber when said slider is moved to one side, said slider being preferably configured for adjusting the flow of air into said rebreathing air chamber by uncover or cover one or more through going opening.

Preferably, such rebreathing air-chamber-connectors may preferably comprise or may preferably further comprise through one or more through going openings, preferably being non-adjustable in size, and allowing fluid communication in and/or out of the rebreathing air chamber with the surrounding atmosphere. Preferably, such rebreathing air-chamber connectors may preferably comprise an elongate unfold element 34 preferably extending slide-able in a direction preferably being perpendicular to the folding lines along a surface of said connector and being fixed at one end to said connector so as to be configured for unfolding the rebreathing air-chamber-connector from its folded configuration by a user pulling in the elongate unfold element at an end being opposite to the end being fixed.

Preferably, such rebreathing air-chamber connectors may preferably comprise guide elements maintaining the elongate unfold element in a guided position on said connector.

Preferably, such the elongate unfold elements and/or such rebreathing air-chamber connectors may preferably comprise a latch configured for latching the elongate unfold element's position when the said rebreathing air-chamber connector is in its unfolded configuration.

Preferably, the rebreathing air-chamber may comprises a strip, such as a pull-tab attached to a wall section of the rebreathing air-chamber allowing a user to expand the rebreathing air-chamber, preferably to unfold the rebreathing air-chamber from a folded configured, so as to make it easier for a user to exhale air into the rebreathing air-chamber.

The individual aspects of the present invention may each be combined with any of the other aspects. These and other aspects of the invention will be apparent from the following description with reference to the described embodiments In the present context, a number of terms are used in a manner being ordinary to a skilled person; however, some of these terms are elucidated below:

Rebreathing air chamber is preferably used to mean/denote the bag of the breathing device.

RBR is preferably used to mean/denote the Rebreathing Ratio, which is the ratio A/B where A is the subset of the inspired air flow consisting of gas which has previously been breathed out and B is the total inspired air flow.

First wall section is preferably used to mean/denote a part of the rebreathing air chamber, being permeable to gas and having a conductance G.

Second wall section is preferably used to mean/denote a part of the rebreathing air chamber, being impermeable to gas and having a compliance C.

G is preferably used to mean/denote the conductance of the wall section(s) of the RC, i.e. the volume flow through the wall section per second per pressure difference across the wall section).

C is preferably used to mean/denote the time-normalized compliance of the wall section(s) of the RC, i.e. the volume expansion of the rebreathing chamber per second per pressure difference across the wall section VDA is preferably used to mean/denote the anatomical dead space inside the body.

VDD is preferably used to mean/denote the rigid dead space of the breathing device's mouthpiece.

$P_{ACO2}$ is preferably used to mean/denote the average alveolar partial pressure of $CO_2$.

$P_{aCO2}$ is preferably used to mean/denote the arterial partial pressure of $CO_2$.

$F_{ICO2}$ is preferably used to mean/denote the inspired $CO_2$ fraction to the lungs.

$\dot{V}_A$ is preferably used to mean/denote the delivery per minute of fresh air to the alveolar space of the lungs.

Slider is preferably used to mean/denote a wall element, configured for providing an opening into the breathing device. The slider may have other shapes, such as rotary valve.

By partly flexible is preferably meant that at least a part of the wall(s) forming the rebreathing air chamber is flexible whereas another part is non-flexible.

BRIEF DESCRIPTION OF THE FIGURES

The figures show one way of implementing the present invention and is not to be construed as being limiting to other possible embodiments falling within the scope of the attached claim set.

FIG. 11.a illustrates an embodiment of the breathing device, in which the rebreathing air chamber is in the form of a cube and comprises a socket and re-closable openings in the flexible wall section.

In FIG. 13 the mouthpiece is shown in an unfolded version.

In FIG. 13 the mouthpiece is shown in an unfolded version, with hinges which the cabinet elements are attached to.

FIG. 16a-c illustrates an aspect of the invention according to which the rebreathing air-chamber connector is foldable preferably to accommodate the rebreathing air-chamber in it folded state.

DETAILED DESCRIPTION OF AN EMBODIMENT

Figure 1:
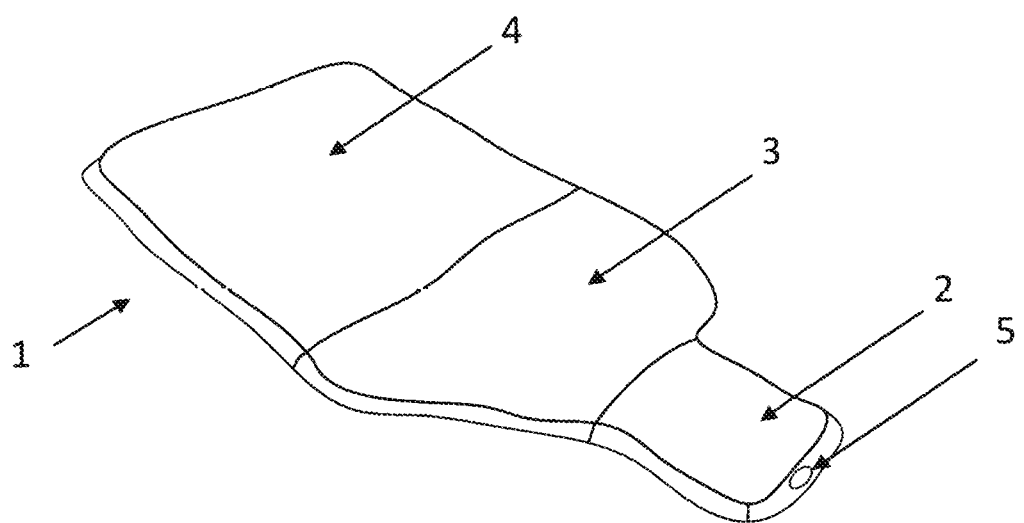
FIG. 1 illustrates a breathing device composed of a rebreathing air chamber and a mouthpiece.

Reference is made to FIG. 1, illustrating a breathing device 1. The breathing device comprises a mouthpiece 2 forming a breathing channel to form a connection between a first end and a second end of the mouthpiece 2. The first end is configured for a user breathing into the mouthpiece through a breathing opening 5. The breathing opening 5 comprises a connection, such as a pipe, duct or other connection, suitable for connecting the breathing device to a facial mask. The mouthpiece 2 is preferably adapted to engage with a user's mouth, so the user breathes into the mouthpiece 2. However, the mouthpiece may also be used as an intermedia between a user's mouth and an additional connector, such as a facial mask, which is connected to the mouthpiece 2.

One embodiment of the breathing device comprises an at least partly flexible rebreathing air chamber 15. The rebreathing air chamber 15 is attached to the second end of the mouthpiece, being in fluid connection with the breathing channel. The rebreathing air chamber is formed by an at least partly flexible wall section(s) having at least a first wall section 3, 10, 11, 16, 28 being permeable to gas by one or more, such as a plurality of pores and/or through going openings 27 provided in the wall section, and/or the mouthpiece 2 comprising one or more through goings openings 19, 35, allowing fluid communication between the breathing channel and the surrounding atmosphere. The plurality of pores are equidistantly disturbed in the at least partly flexible wall sections(s). The hydraulic diameter of the pores is smaller than 2 cm, such as smaller than $10^{-2}$ m, such as smaller than $10^{-3}$ m, preferably equal to or smaller than $180*10^{-6}$ m.

Another embodiment of the breathing device comprises a rebreathing air chamber 15. The rebreathing air chamber is attached to the second end of the mouthpiece, being in fluid connection with the breathing channel. The rebreathing air chamber comprises a number of holes in the wall section 3, these holes being permeable to gas and having a combined conductance G (i.e. a measure of the volume flow through the wall section per second per pressure difference across the wall section). The material of the wall section 3 is impermeable to gas (i.e. gas can only flow through the holes in section 3 and does not diffuse through the material), the wall section having a time-normalized compliance C (time-normalized compliance being a measure of the volume expansion of the rebreathing chamber per second per pressure difference across the wall section). It is desirable to design the device with a C value and a range of adjustable G values, such that a given user (having individual values of tidal volume, breathing rhythm and $V_{RC,EI}$ when using the device) will obtain an RBR between 0.5 and 0.9, such as between 0.5 and 0.95.

In another embodiment of the breathing device, the rebreathing air chamber comprises a first wall section 3 being permeable to air and a second wall section being impermeable to air 4.

Figure 7:
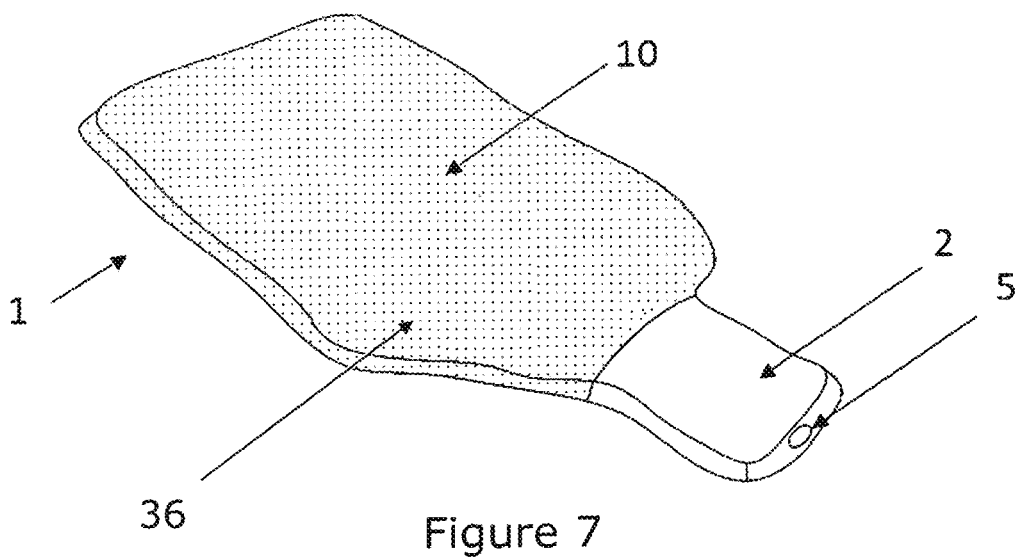
FIG. 7 illustrates an embodiment of the breathing device, in which the entire wall of the rebreathing air chamber consists of the same hole-perforated material, equally distributed.

The rebreathing air chamber 15 may be formed by the flexible wall section 3 and/or flexible second wall section, which are permeable to gas by a plurality of pores and/or through going openings provided in the wall section 3. This embodiment of the rebreathing device is illustrated in FIG. 7. The pores and/or through going openings provides a fluid communication from the rebreathing air chamber to the surrounding atmosphere.

Figure 8:
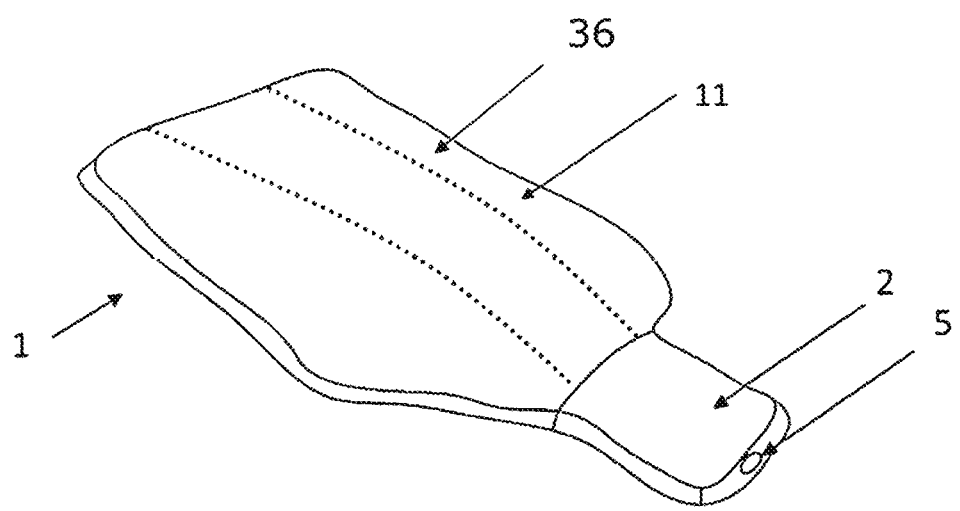
FIG. 8 illustrates an embodiment of the breathing device, in which the wall of the rebreathing air chamber is perforated by pores arranged in two lines.

In another embedment of the present invention, the rebreathing chamber 15 may by formed by the flexible wall section 11, which is permeable to gas by a plurality of pores and/or through going openings arranged in lines or rows, distributed in the flexible wall section 11. This embodiment is illustrated in FIG. 8, which illustrates an embodiment of the breathing device, in which the pores and/or through going openings is arranged in two lines in the flexible wall section 11. However, the flexible wall section may comprise one line of pores and/or through going openings, or two or more lines of pores and/or through going openings. The lines may be arranged longitudinal in the flexible wall section 11 as shown in FIG. 8, or crosswise (not shown in the figure).

In another embodiment of the present invention, the breathing further comprises an rebreathing air-chamber-connector 26. The connector 26 is configured
for connecting a facial mask or said mouthpiece 2 to the rebreathing air chamber 15, or
so that said connector 26 forms the mouth piece 2.

At least a part 28 of the connector forming at a least part of the first wall section and/or second wall section. The rebreathing-air-chamber-connector 26 allows fluid communication in and/or out of the re-breathing air chamber 15 with a user's breath.

The rebreathing air chamber 15 may be formed by one the following forms: cube, such as cuboid, sphere, such as spheroid, bag type, tetrahedron, such as substantially tetrahedron, square-based pyramid such as substantially pyramid, octahedron, such as substantially octahedron, hexagonal prism such as substantially prism, dodecahedron, such as substantially dodecahedron, cylinder, or cylindroid. The basic idea is to minimize the distance from the breathing channel to any point on the wall of the rebreathing air chamber. By not constructing for a minimal distance to all points on the wall of the rebreathing air chamber, support structures must be put in place in order to avoid collapse of the bag over the second end of the mouthpiece 2 during inhalation.

In another embodiment of the present invention, the form of rebreathing air chamber 15 is selected according to any of the above-mentioned shapes. The rebreathing air chamber comprising panels each defining a face of the rebreathing air chamber. One or more of the panels and/or at least a part of one of the panels form the first flexible wall section, and at least one of the panels form at least a part of the second flexible wall section 18. The first wall section preferably comprises permeable sections or being permeable to gas by a plurality of pores and/or through going openings preferably arranged in lines or rows, distributed in the flexible first wall section.

Figure 10:
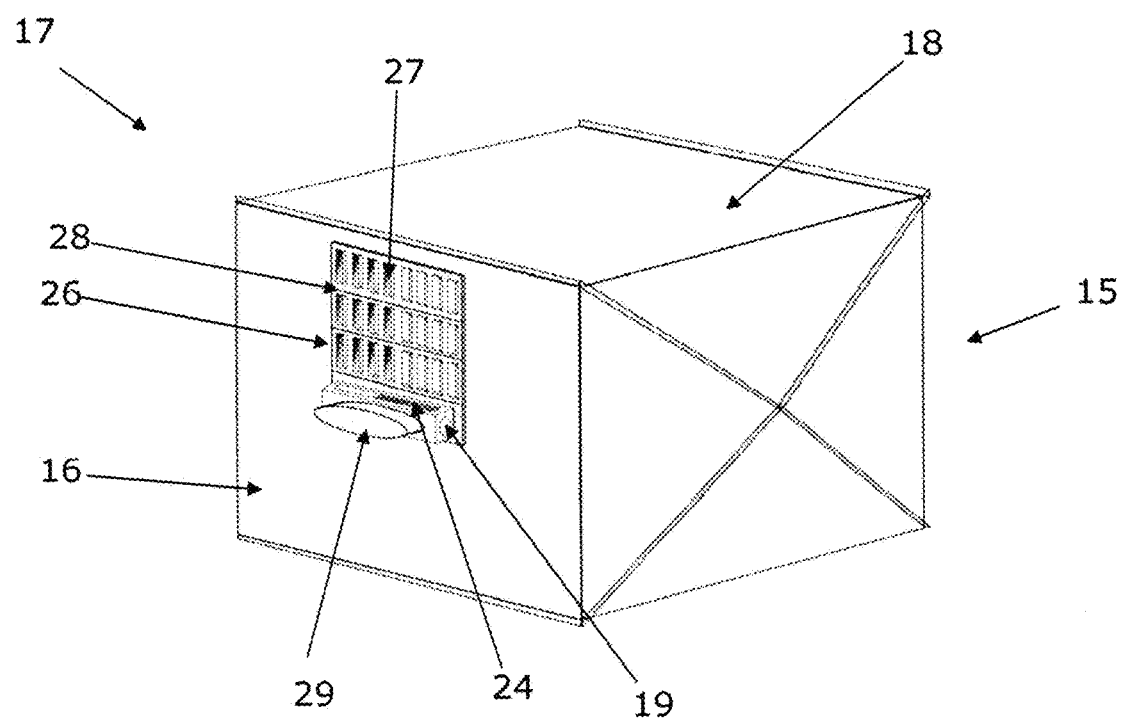
FIG. 10 illustrates an embodiment of the breathing device, in which the rebreathing air chamber is in the form of a cube.

In FIG. 10, the rebreathing air chamber 15 is schematically illustrated in the form of a cube, such as a cuboid. The cube, such as cuboid shape, is formed when the user inflates the rebreathing air chamber.

In another embodiment, wherein the rebreathing air chamber is in the form of a cube, such as cuboid, one or more of the panels comprises a first flexible wall section and second flexible wall section. The panels and/or wall sections may have a thickness smaller than 4 mm, such as smaller than 2 mm, such as smaller than 1 mm.

In another embodiment (not shown in the figures), the first wall section 16 and second wall section 18 may be impermeable to gas. This embodiment of the breathing device requires through going openings 19 arranged in the mouthpiece 2.

Figure 11:
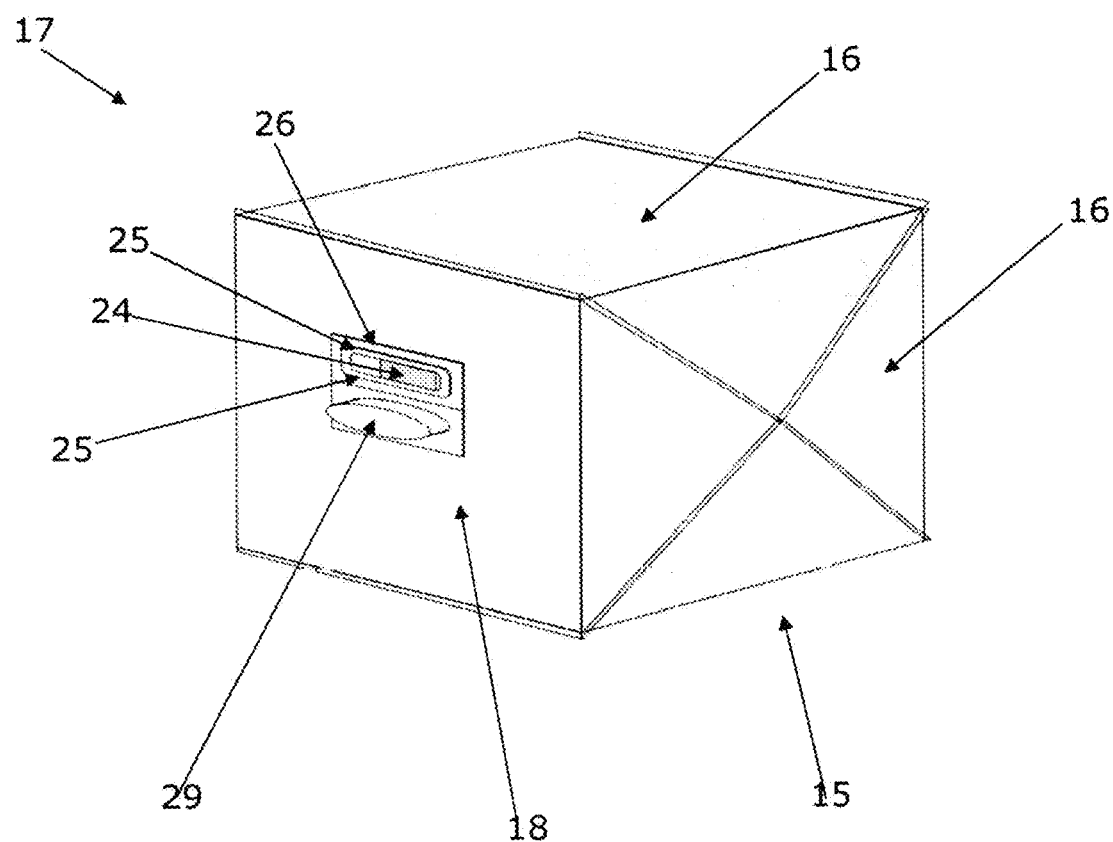
FIG. 11 illustrates an embodiment of the breathing device, in which the rebreathing air chamber is in the form of a cube and comprises a socket and a slider in the flexible wall section.

In the embodiments of the present invention, wherein the rebreathing air chamber is in the form of a cube, as illustrated in FIGS. 10 and 11, the permeable sections of the flexible first wall section type 16 preferably has a thickness smaller than $10^{-2}$ m, such as smaller than $10^{-3}$ m, preferably equal to or less than $20*10^{-6}$ m. The flexible first wall section type 16 may further comprise impermeable sections having a thickness smaller than $10^{-2}$ m, such as smaller than $10^{-3}$ m, preferably equal to or less than $40*10^{-6}$ m. The impermeable second flexible wall section type 18 may have a thickness smaller than $10^{-2}$ m, such as smaller than $10^{-3}$ m, preferably equal to or less than $40*10^{-6}$ m.

The rebreathing air chamber may be permeable or impermeable.

The second wall section 18, where the breathing channel is arranged, may be thicker than the first wall section 16, so as to ensure that the wall section 18 doesn't collapse under use, and hereby prevents the flow of fluid from the rebreathing air chamber to the breathing channel.

The embodiments of breathing device illustrated in FIGS. 10 and 11, may further comprise a breathing channel arranged in the rebreathing-air-air chamber-connector 26, allowing fluid communication in and/or out of the rebreathing air chamber 15 with the user's mouth, during use. The breathing channel may be configured for connecting a connection, such as a pipe, duct or other connection, suitable for connecting the breathing device to a facial mask. This configuration, allows the rebreathing air chamber 15, to be entirely impermeable. However, in an another embodiment of the present invention, the same setup can be used, with the rebreathing air chamber 15 being partly permeable.

The breathing channel may further comprise at least one through going opening 19, allowing fluid communication in and/or out of the breathing device with the surrounding atmosphere, as shown in FIGS. 10 and 11. These through going openings may be re-closable and/or adjustable in size, e.g. by a valve mechanism, so the user can adjust the flow of air in and/or out of the breathing device, by closing or opening some of the through going openings manually. The through going openings 30 provided in the breathing channel may be covered by a slider 24, arranged between two parallel longitudinal wall sections as illustrated in FIG. 10 or 11. The slider provides an opening 30 into the breathing channel 2, when the slider 24 is moved translator between the two parallel longitudinal wall sections 25. The user may adjust the flow of air into the rebreathing air chamber 15 by moving the slider a distance to one side.

Figure 12:
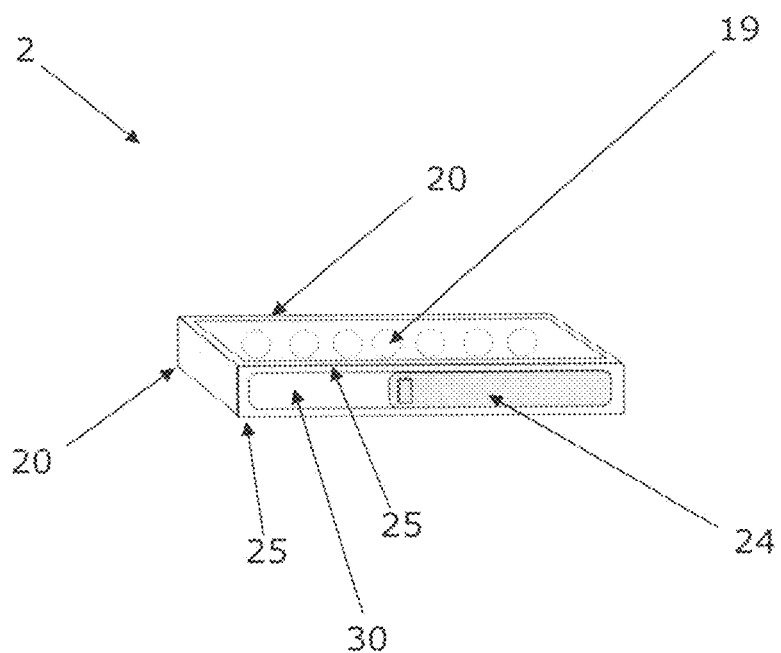
FIG. 12 schematically illustrates the mouthpiece, comprising a slider and through going openings.

The breathing channel may further comprise two parallel longitudinal wall sections 20, shown in FIG. 12, protruding in a perpendicular direction to a breathing direction to the breathing channel. The distance in between the two parallel longitudinal wall sections is preferably below 3 cm, such as below 2 cm preferably below 1 cm. This arrangement of the two parallel wall sections 20 prevents the user from blocking the through going openings with a finger, while holding the breathing device with the fingers. The through going openings 19 is arranged in between the two parallel longitudinal wall sections 20. The two parallel longitudinal wall section is a security feature, to prevent the user from blocking the air flow in and/or out from the breathing device.

In another embodiment of present invention, the rebreathing air chamber comprises non-adjustable through going openings 27, arranged on the rebreathing-air-chamber-connector 26 allowing fluid communication in and/or out of the rebreathing air chamber with the surrounding atmosphere.

FIG. 11 illustrates an embodiment of the present invention, wherein the breathing air chamber 15 comprises a socket 29 configured for connecting the rebreathing air chamber to the mouth pieces while allowing fluid communication in and/or out of the rebreathing air chamber, and one or more re-closable and/or adjustable openings, preferably comprises a slider 24 arranged between two parallel longitudinal wall sections 25. The slider is arranged on the flexible wall section 18, and the slider provides an opening into the breathing air chamber 15 when said slider 24 is moved to one side between the two parallel longitudinal wall sections 25. The slider 24 is configured for adjusting the flow of air into said rebreathing air chamber 15. The socket 29 is a part of the rebreathing-air-chamber-connector 26 and is configured for connecting to a facial mask or a mouthpiece. The rebreathing-air-chamber-connector 26 is an intermedia between the rebreathing air chamber 15 and the mouthpiece.

Permanently or temporarily connected with rebreathing bag using glue or welding. The rebreathing-air-chamber-connector 26 is connected with rebreathing air chamber with a snap lock. The rebreathing-air-chamber-connector 26 may be made of PP, PE or bio-degrable material. The connector can be folded or manipulated so that it can hold the rebreathing air chamber in a compact way. This means that the connector 26 can be used as its own packaging for the rebreathing air chamber.

In this embodiment of the present invention the breathing channel/mouthpiece and the slider is arranged independently from each other on the flexible wall section 18, as shown in FIG. 11.

In another embodiment of the present invention, the socket 29 forms the mouth piece 2, so the user may breathe into the rebreathing air chamber through the mouthpiece.

As illustrated in FIG. 11.*a*, the rebreathing-air-chamber connector 26 comprises non-adjustable through going openings 27 allowing fluid communication in and/or out of the rebreathing air chamber with the surrounding atmosphere. The through goings openings 19, 27 are configured for directing the outgoing fluid from the rebreathing air chamber away from the users face.

In the figures the through going openings 19, 27 are illustrated as having a round or roundly shape, however the through going openings 19, 27 may be in rectangular and/or elliptical form.

The hydraulic diameter of the through goings openings 19, 27 is $100*10^{-6}$ m to 2 cm per through going opening 19,27.

The flexible wall sections 16, 18 may be foldable such as pleated according to the embodiments of the present invention illustrated in FIGS. 10 and 11.

The rebreathing air chamber 15 illustrated in FIGS. 10 and 11, may be assembled by a plurality of panels, welded together to form a cube.

Another way of assembling the cube, is by four panels being formed by two triangular wall elements arranged on opposite to each other sides of one square wall element. The two triangular wall elements is an extension of the square element, and is a not welded to the square element. These four panels are welded together to form the cube. Because of this construction, the impermeable wall sections 16 will comprise permeable sections, as a consequence of the permeable wall section 18, which has two triangular wall element being a part of the wall section 16.

On FIG. 11, the part extending from the welding point of wall sections 16 and 18, is an excess part of wall section 18. On the side opposite to the wall section 18, the part extending from the welding point of the two wall sections 16, is an excess part of the wall section 16.

In another embodiment of the present invention, the plurality of pores and/or through going openings are equidistantly disturbed in the first flexible wall sections 10. The hydraulic diameter of the pores and/or through going openings is smaller than 2 cm, such as smaller than $10^{-3}$ m, preferably equal to or smaller than $180*10^{-6}$ m.

The breathing opening 5 may also be used so as to engage with a user's mouth, so the user breathes into the breathing opening 5.

The rebreathing air chamber 15 may be detachably attached to the breathing channel 2.

In another embodiment of the present invention, the breathing opening 5 comprises a connection, such as a pipe, duct or other connection, preferably suitable for connecting the breathing device to a facial mask.

The first wall section 3 and/or second wall section are wholly or partially hydrophobic.

The rebreathing air chamber 15 has a volume between 1 liter and 16 liter, such as 2 liter and 8 liter, preferably between 4 liter and 6 liter, and is volumetrically sizeable by changing the geometry of the rebreathing air chamber and/or the permeability of the first wall section is sizeable. By changing the geometry of the rebreathing air chamber, the user can adjust the amount of pores and/or through goings openings being in fluid communication with the surrounding atmosphere.

The first wall section 3 and/or second wall section are foldable, such as pleated.

The breathing channel 2 has a cross-section of at least 1.0 cm$^2$, such at least 1.5 cm$^2$, preferably at least 2.0 cm$^2$. The breathing channel 2 may, in another embodiment of the present invention, comprise more than one internal channel in the breathing channel 2.

The first wall section 3, 10, 16 has an average pore and/or through going openings size between about 2 nanometers and 2 millimetres, or preferably above 2 mm.

The pores and/or through going openings are made by laser perforation.

The permeable material has a gas permeation flux for standard air determined at 20° C. and standard atmosphere (101.325 kPa), wherein the gas permeation flux is at least about 0.0005 m3/(sec*m2*kPa) and a pressure difference between the interior of the rebreathing air chamber and the surrounding atmosphere being between 5 and 35 Pascal.

The permeable material comprises a polymer membrane, comprising polytetrafluoroethylene (PTFE), perfluoroalkoxy (PFA), fluorinated ethylene propylene (FEP), polyvinylidene difluoride (PVDF), polyethylene (PE), polypropylene (PP), paper, vegetable fibres, bio-degradable material and/or combinations comprising any of the above mentioned polymers. By bio-degradable material is meant, a material which is capable of being broken down (decomposed) rapidly by the action of microorganisms.

At least a part of the rebreathing air chamber 15 is non-collapsible, preferably, at least a part of rebreathing air chamber 15 is non-collapsible and a part of the rebreathing air chamber 15 is collapsible. More preferably the rebreathing air chamber, 15 is partly collapsible and at least a sub-compartment closer to the breathing opening 5 into the rebreathing air chamber 15 is not collapsible or at least less collapsible than a sub-compartment farther from the breathing opening 5. This feature ensures a collapsing of the rebreathing air chamber when the user sucks fluid out of the rebreathing air chamber.

The rebreathing air chamber will always be "at rest" so that it does not change shape after having been "manipulated". I.e. the user can pull the rebreathing air chamber and it will keep that pulled shape after the user let it go.

The rebreathing air chamber may comprise rigid parts that go into the rebreathing air chamber and pushes the rebreathing air chamber away from the opening. This could be a small shade like object that ensures that it is difficult for the rebreathing air chamber to get sucked into the cabinet/mouthpiece on inhalation.

At least one through going opening (not shown in the figures) is provided in the breathing device, allowing fluid communication in and/or out of the breathing device with the surrounding atmosphere. The through going opening may preferably be provided in the mouthpiece 2 facing downwardly or upwardly during use. The through going is arranged in a distance from the breathing opening to avoid being obstructed by e.g. clothes, fingers or the like.

One or more of the at least one through going opening is provided with a valve, preferably an adjustable valve for regulating the gas flow through the aperture. The adjustable valve is automatically adjusted. The valve is adjusted so as to provide a desired RBR.

The rebreathing air chamber 15 may comprise a valve for draining off condensed water.

In a preferred embodiment (not shown), the breathing device comprises a $CO_2$ or $O_2$ sensing device incorporated into the breathing device, configured to measure the $CO_2$ and/or $O_2$ level of the inhaled and/or expired air. Such a sensor can be used to monitor whether the $CO_2$ exceeds or falls below a certain limit and/or the $O_2$ level is below a certain limit and if either of these situations occurs, a warning may be signalled to the user. If such a warning is signalled, the valve of the through going openings in the mouthpieces can be set to increase/decrease the flow going through thereby altering the amount of gas being expelled/inhaled through the through going opening.

In another embodiment (not shown), the breathing device comprises a $O_2$ sensing device incorporated into the breathing device, configured to measure the $O_2$ level of the users blood, through the surface of the users skin.

A preferred embodiment of the breathing device comprises at least one moisture-absorbing element configured to absorb moisture from the rebreathing air chamber 15. The moisture absorbing element(s) are at least partly placed in the rebreathing air chamber 15. Such a moisture-absorbing element may be a removable and replaceable element.

The breathing device may comprise a flavouring device, such as flavouring to have the flavour of menthol, configured to change the odour of the rebreathing gas.

The first and/or second wall section 4 may comprises a water-transporting element configured to drain off water from the rebreathing air chamber 15. The water-transporting element is made from or comprises a material which provides a path for transporting water from the rebreathing air chamber 3, 4 to the surrounding atmosphere or to a water-collecting unit.

The breathing device may further comprises a cabinet 9, 21, 22 inside which a part of the mouth piece 2, such as the trough gong opening(s) and/or slider, and the rebreathing air chamber 15 is stored when not in use. The mouthpiece can form the cabinet and vice versa.

The mouthpiece 2 and the rebreathing air chamber 15 is/are replaceable such as repositionally arranged in the cabinet.

Figure 5:
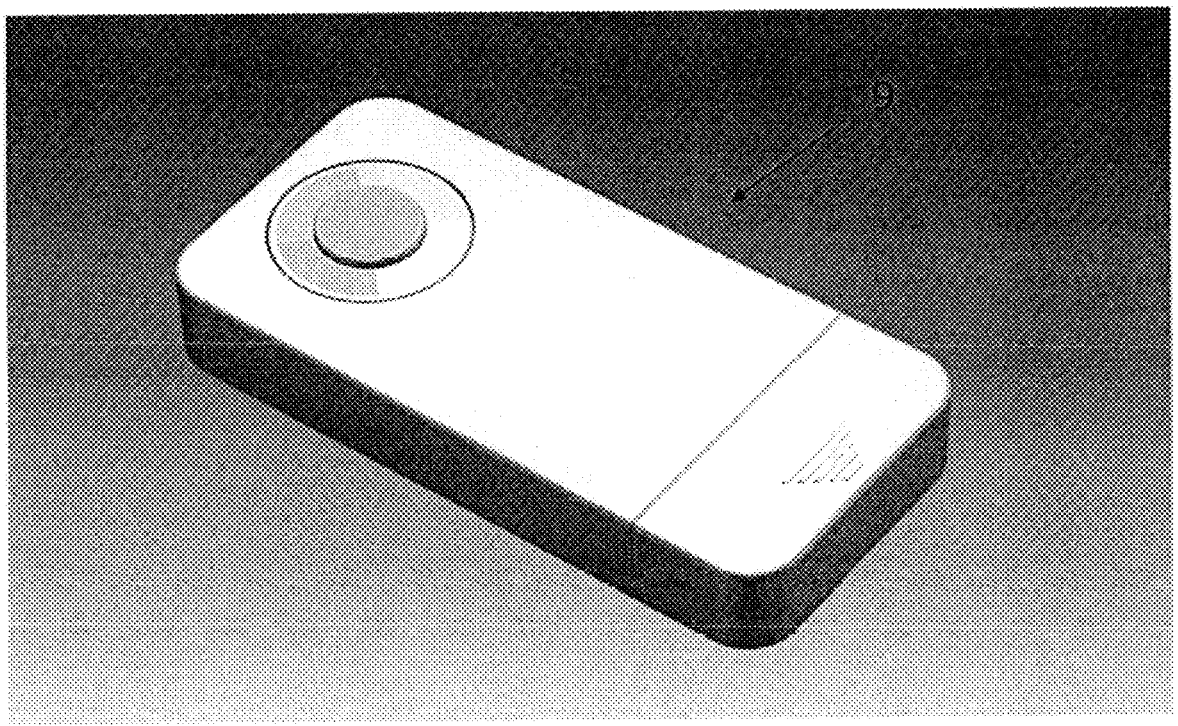
FIG. 5 illustrates a cabinet, in which the rebreathing air chamber and mouthpiece can be stored.

FIG. 5 illustrates the cabinet 9, in which the rebreathing air chamber and a part of the mouthpiece can be stored. The rebreathing air chamber can be folded and placed inside the cabinet. The mouthpiece can be covered by a lid.

Figure 6:
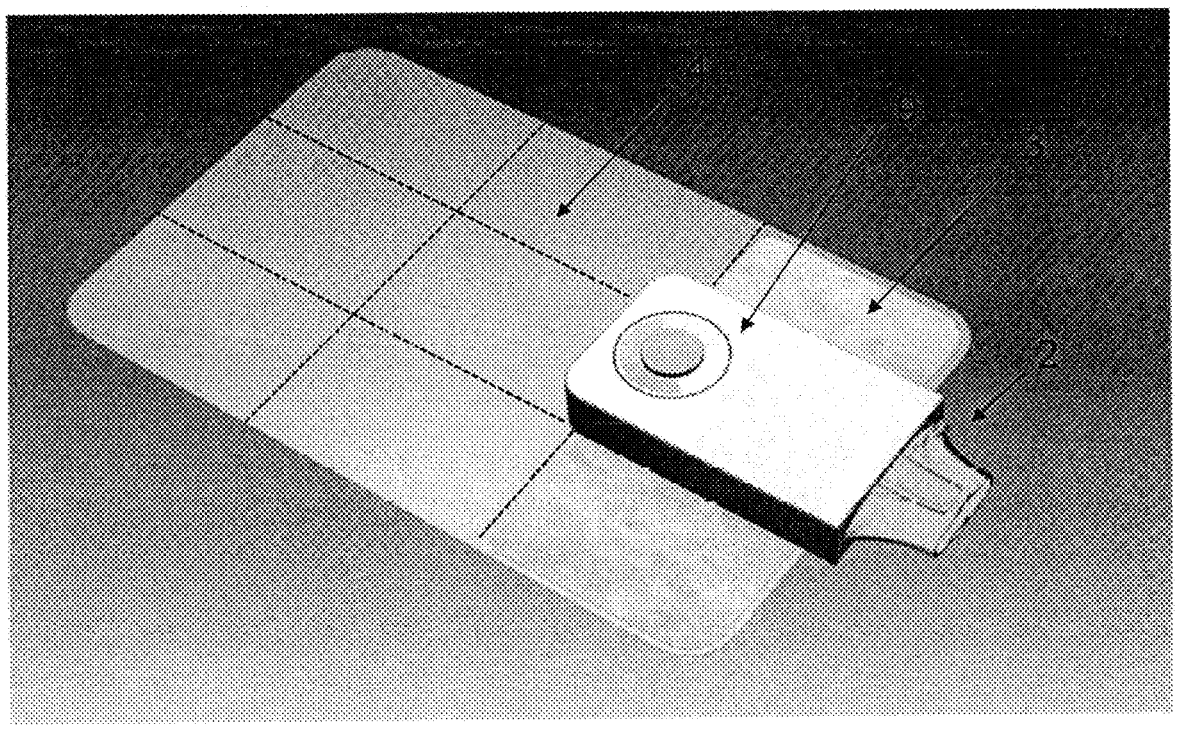
FIG. 6 illustrates a cabinet, in which the rebreathing air chamber and mouthpiece are shown in an unfolded version.

In FIG. 6, a version of the cabinet 9 is shown, wherein the rebreathing air chamber is in an unfolded version. The rebreathing air chamber is—when in folded state—folded along the folding lines illustrated in FIG. 6 by dotted lines.

Thereby the folded rebreathing air chamber has a width and a breadth being slightly smaller than the width and the breadth of the cabinet's lower side allowing the folded rebreathing air chamber to be accommodated inside the cabinet and covered by the lid. Further, by removing the lid (see FIG. 5) the mouthpiece will be exposed.

Figure 13:
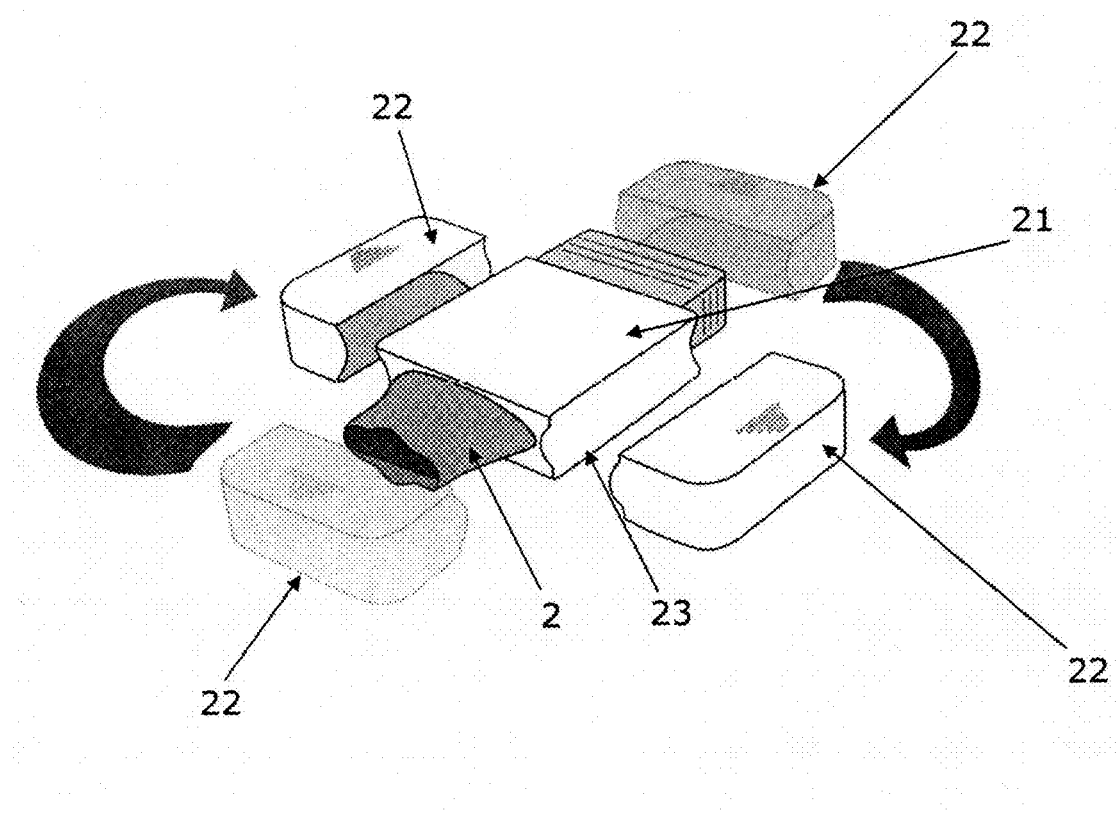
FIG. 13 schematically illustrates the cabinet in which the rebreathing air chamber and mouthpiece is stored during non-use.

In FIG. 13 another embodiment of the cabinet 21 is illustrated. The cabinet comprises two detachable cabinet elements 22, such as lids, each replaceable such as repositionally to an end of the cabinet 21. The two detachable cabinet elements is configured for preventing access to either said rebreathing air chamber 15 or breathing channel 2 when device is not in use. The detachable cabinet elements 22 is configured to provide access to said rebreathing air chamber 15 and/or to said breathing channel 2 when detached or replaced such as repositioned.

The cabinet elements 22 are configured for being replaced, such as repositioned on two sides 23 adjacent to the ends where there is access to either the rebreathing air chamber 15 or breathing channel 2 during non-use, so as to provide a better grip on the breathing device in use. This is illustrated in FIG. 13 by arrows pointing out the direction of the cabinet elements 22 when replaced to the sides 23. When the breathing devise is not in use, the lids 22 is arranged on the cabinet 21, to cover the mouthpiece 2 and the rebreathing air chamber. When the breathing device is in use, the lids may be manually transferred to the two sides 23, so the user can provide a better grip on the breathing device.

When replaced, the cabinet elements cover both a part of mouthpiece and rebreathing air chamber and ensures that the mouthpiece stays clean and that the rebreathing air chamber-connector and rebreathing chamber stays intact. It also ensures that the breathing device can be transported with everything needed inside the device.

Figure 14:
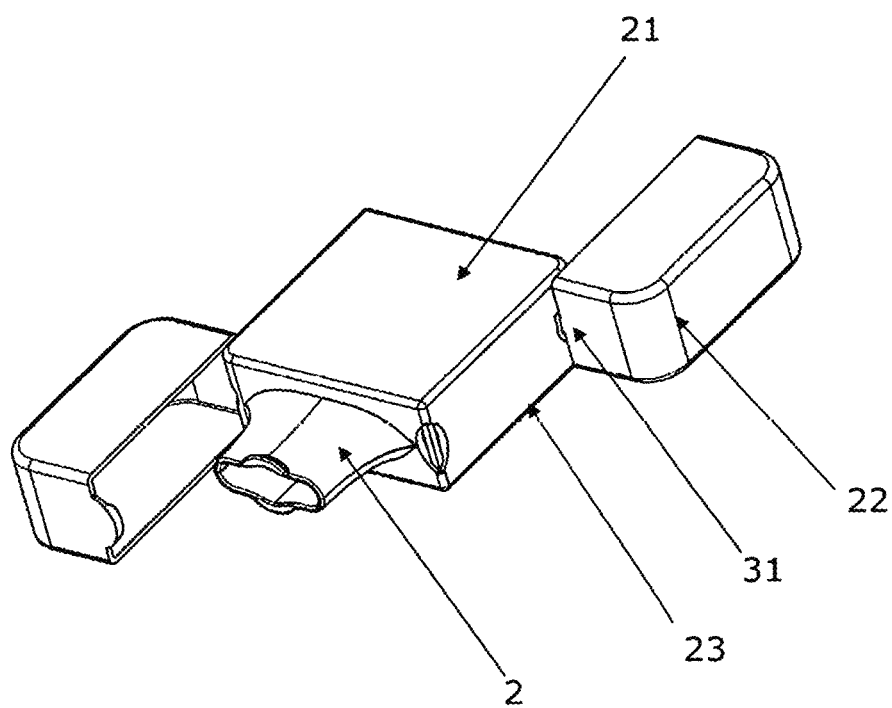
FIG. 14 schematically illustrates the cabinet in which the rebreathing air chamber and mouthpiece is stored during non-use.
Figure 15:
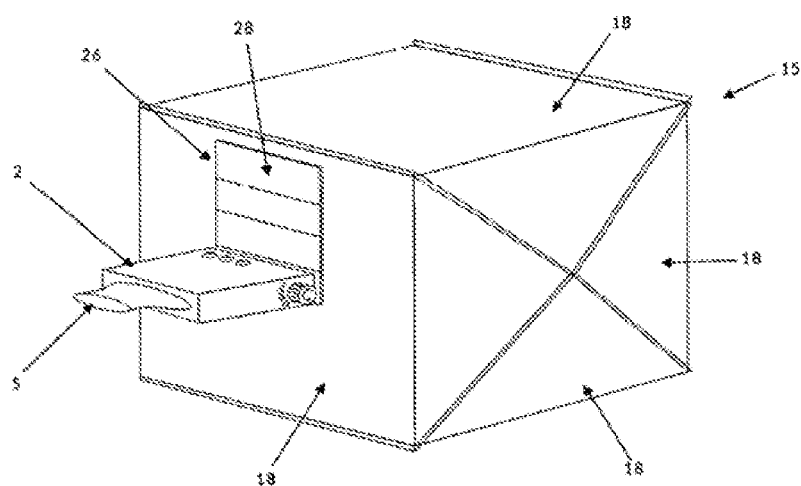
FIG. 15 illustrates an embodiment of the breathing device, in which the rebreathing air chamber is in the form of a cube and comprises a mouthpiece and re-closable openings in the form of an valve in the mouth piece as well as static through openings in the mouth piece.

FIG. 14 hinges schematically another embodiment of the cabinet 21, wherein the hinges 31 are schematically illustrated. The hinges ensures that the cabinet elements can only be replaced, such as repositioned, on the two sides. Through going openings 19 (not illustrated) may be provided in the cabinet 21 leading into the breathing channel formed inside the cabinet 21.

Another embodiment of the breathing device is illustrated in FIG. 7, in which the entire wall of the rebreathing air chamber consists of the same hole-perforated material 10, i.e. with no distinction between a permeable and non-permeable wall section 3, 4.

Another embodiment of the breathing device is illustrated in FIG. 8, in which the flexible wall section 11 of the rebreathing chamber is perforated by two lines of pores/holes.

In the embodiments shown in FIGS. 7 and 8, the perforations/pores/holes in the wall provide the flow connection to the atmosphere having the conductance G, while the non-perforated wall material provides the expandable volume characterized by the conductance $G_{expan}$ or compliance C.

In another embodiment of the present invention, the rebreathing air chamber 15 is detachable from, and de-attachable to, the mouth piece 2.

Figure 9:
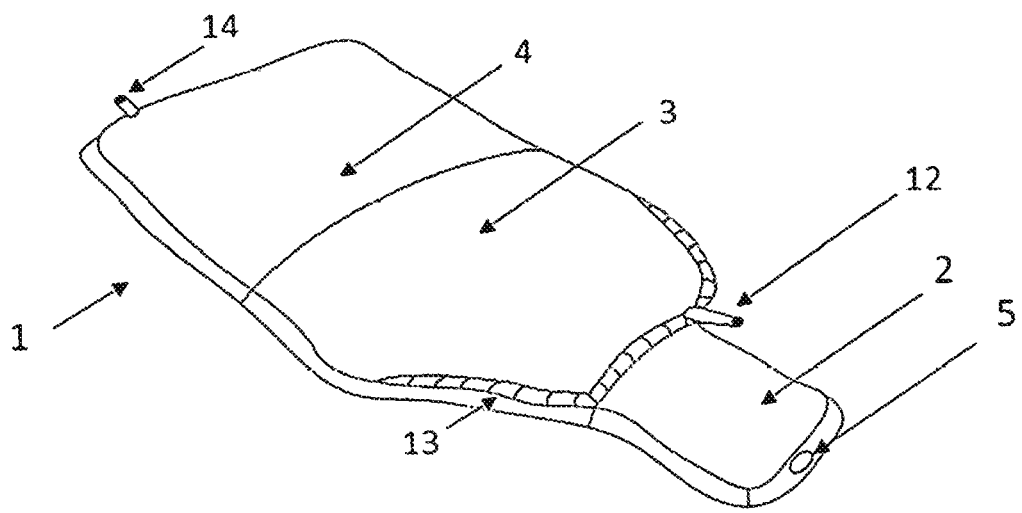
FIG. 9 illustrates an embodiment of the breathing device comprising a structural stability chamber and one-way deflation valve.

In another embodiment of the invention, illustrated in FIG. 9, the device comprises a second air chamber, the structural stability chamber (13), attached (but not in direct fluid connection to) to the rebreathing air chamber 15.

The second chamber is a pressurised chamber thereby securing suitable and sufficient structural stability and rigidity to prevent complete collapse of the rebreathing air chamber during the inhalation phase of the rebreathing, thereby preventing that such a collapse leads to blockage of the distal end of the mouth piece (2) and/or blockage of the permeable sections of, or pores in, the wall of the rebreathing air chamber. While in its pressurized state, the structural stability chamber secures permanent and unobstructed airflow between A) the mouthpiece and B) the rebreathing air chamber and any pores and/or filter material in its wall. This is accomplished by creating a standing dead-space of approx. 0-10% of the maximum volume of the rebreathing bag.

Activation of the structural stability chamber is initiated before use of the rebreathing device, by air supplied by the user exhaling through the mouthpiece (2) and/or through a bellows or non-return valve (12) attached to the structural stability chamber and/or the mouthpiece. By exhalation of air into the valve, or by activation of the bellows, the structural stability chamber is pressurized causing it to expand.

Optionally, the non-return valve (12) inflating the structural stability chamber may be placed inside the mouth piece (2).

The non-return valve is preferably made from same material as the non-permeable wall of the rebreathing air chamber or could be a moulded design. The functionality and efficiency of the non-return valve is based on the pressure difference between the atmospheric pressure acting on the outside of the structural stability chamber and the pressure inside the structural stability chamber. Changes in the atmospheric air pressure may lead to changes in the volume of the structural stability chamber, in which case it may be desirable for the user to deflate or further inflate the structural stability chamber by means of the non-return valve.

The structural stability chamber may have a conical design with diminishing dimension from the proximal to the distal end (proximal/distal being defined in relation to the breathing opening (5).

The embodiment of the breathing device illustrated in FIG. 9, also includes one or more additional non-return valves (14) ("deflation valve(s)") connected to the rebreathing air chamber, 15.

At the end or finalisation of use of the rebreathing device, the deflation valve(s) allow(s) a user to easily empty the device's air chambers of air, in practice by compressing the air chambers by finger touch and thereby producing a pressure increase inside the chamber which expels the air through the deflation valves. Such deflation valves thereby help to ensure that the structural stability chamber and/or rebreathing air chamber can be emptied to regain the full flexibility and further flattened to secure repackaging into the cabinet (9) in a storage position.

Further to the two deflation valves, a third valve (not shown in FIG. 9) can be placed in the distal end of the rebreathing chamber to enable removal or tapping of accumulated fluids developed during condensation on the inside walls of the rebreathing air chamber.

In another embodiment the structural stability chamber walls are made of an elastic material and comprise a shut-off valve (not shown in FIG. 9) providing a fluid and adjustable connection to the outside atmosphere, the elasticity of the wall material allowing for automatic and instant collapse of the structural stability chamber once the shut-off valve is opened.

Functionality

The following section is not intended for limiting the scope of the invention, but is presented in order to provide presentations/indications on the physics involved in using preferred embodiments of a breathing device according to the present invention.

The user breathes into/through the mouthpiece 2. The wall of the rebreathing air chamber is partially made from a semi-permeable material and partially from a non-permeable material, alternatively by a material which is perforated by holes. In use, part of the expired flow from the user enters the rebreathing air chamber and the rest enters the atmosphere through the first wall section 3. When the user inhales, the air collected in the rebreathing air chamber is re-inspired along with some fresh air entering from the atmosphere through the first wall section, reducing the amount of inspired fresh air per minute (the alveolar ventilation) compared to when the user is not using the device. The ratio A/B is denoted the Rebreathing Ratio (RBR), A being the subset of the inspired air flow consisting of gas which has previously been breathed out and B being the total inspired air flow.

Alternatively, the amount of inspired "bag air" (air from the rebreathing air chamber 15) divided by the total ventilation (total ventilation=inspired bag air+inspired fresh air) may be defined as the Rebreathing Ratio (RBR).

Without being bound by theory, it is believed that by use of the breathing device, it is possible to attain a steady state in which the inspired and bodily $CO_2$ level is raised into the range desired (inspired $CO_2$ fraction (FICO2) 1-6%) while the oxygen saturation is only decreased slightly (less than 5 percentage points).

The increase in $P_{aCO2}$ is achieved by lowering the alveolar ventilation ($\dot{V}_A$=delivery of fresh air to the lungs), as per the physiological approximation:

$$P_{aCO2} \sim P_{ACO2} = \frac{0.863 * \dot{V}_{CO2}}{\dot{V}_A} \qquad (1)$$

($P_{ACO2}$=alveolar partial pressure of $CO_2$, $\dot{V}_{CO2}$=$CO_2$ production pr. min. (mL/min)).

According to equation (1), an increase in $P_{aCO2}$ by 30% can be accomplished by lowering the alveolar ventilation by 23%, though the exact change in $P_{aCO2}$ may differ somewhat depending on the person.

There exists several ways to decrease the alveolar ventilation in a patient. Firstly, a change in breathing rate and/or depth can be effected by a conscious effort by the patient (if he/she is indeed conscious) or—for mechanically ventilated patients—by regulation of the ventilator settings.

Another method is by increasing the patient's dead space $V_D$ (i.e. the air volume of the airways that does not take part in gas exchange with the blood) by a fixed volume, as in the case of snorkel, as can be deduced from the formula for calculating $\dot{V}_A$:

$$\dot{V}_A = f_R * (\dot{V}_T - \dot{V}_D) \qquad (2)$$

($f_R$=respiratory frequency (min$^{-1}$), $V_T$=tidal volume (i.e. the volume of one exhalation)).

A third option is to increase the dead space by a variable volume, for instance by means of a bag or other air variable-volume chamber/reservoir, the volume of which can vary according to the pressure and/or mass of gas inside it. In such a variable-volume rebreathing device, it is necessary to provide a connection to a source of an oxygen-rich gas (such as the atmosphere or an oxygen-rich gas mixture), if the increase in $P_{aCO2}$ is intended to attain a steady non-increasing level and the oxygen saturation in the user's blood is not to drop continuously while using the device.

The overall purpose of the breathing device is to increase the user's arterial partial pressure of $CO_2$ ($P_{aCO2}$) by up to 30%, in order to increase oxygen delivery to the brain and/or decrease the excitability of the nervous system.

If $P_{aCO2}$ has a normal value (40 mmHg) at the outset, an increase of $P_{aCO2}$ of 25% to 50 mmHg will increase cerebral blood flow (CBF) by approximately 70%, increasing oxygen delivery to the brain and counteracting any local or global cerebral oxygen deficiency.

Additionally, by raising $P_{aCO2}$, respiratory acidosis is induced, which, without being bound by theory, leads to a strong decrease in the excitability of the nervous system.

The breathing device may be used in the treatment of migraine.

The breathing device may be used in the treatment of epilepsy.

The breathing device may be used in the treatment of febrile seizures.

The breathing device may be used in the treatment of post-spinal headache.

The breathing device may be used in general to raise the bodily $CO_2$ levels and lower the pH values of the bodily fluids.

The breathing device may be used in the preventive treatment of asthma.

The breathing device may be used in the treatment and rehabilitation of Cardiac arrest.

Description of the Physics

Figure 2:
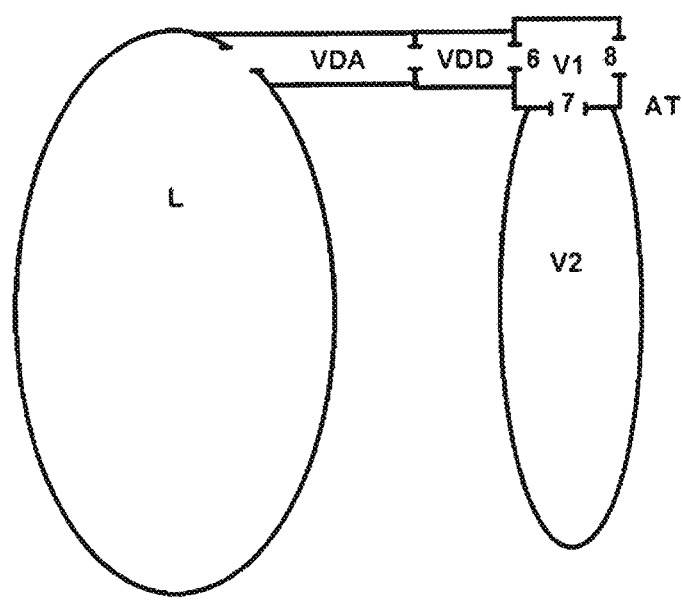
FIG. 2 illustrates a conceptual diagram of the flows in the breathing device.

A conceptual diagram of the flows in the breathing device is illustrated schematically in FIG. 2.

In FIG. 2, the lungs of the device user are represented as L, being in fluid connection with the anatomical dead space inside the body (VDA), which by means of the mouth connects to the rigid dead space of the device's mouth piece (VDD) which by means of flow opening 6 is in fluid connection with the rebreathing air chamber. The volumes L and V2 are of flexible size and oscillate with the ventilation rhythm (i.e. at end of exhalation L is small and V2 is large and vice-versa at end of inspiration). For the purposes of a conceptual analysis of the flows, the rebreathing air chamber can be divided into two constituent sub volumes: a flexible volume V2 with an internal pressure equal to the atmospheric pressure, and a flow dividing sub volume of a fixed small volume V1. Though the boundary between V1 and V2 is in reality fluid and gradual, V2 can be considered as the volume of the rebreathing air chamber close to the wall and V1 as the volume just distal to the distal opening of the mouthpiece. V1 is connected to the atmosphere AT by the flow opening 8, which may be a single hole, a multitude of holes, a membrane, a filter or another type of flow connection. Flow opening 7 may be an actual flow restriction but is here considered a conceptual representation of the resistance to expansion of the rebreathing air chamber.

When the user breathes out, his or her exhaled gas will flow from L and VDA to VDD and into V1. The consequent increase of mass in volume V1 will increase the pressure in V1 above the atmospheric pressure. If the resistance to flow through flow opening 8 (e.g. through the first wall section into the atmosphere) is much larger than the resistance to expansion of V2 (the latter flow resistance symbolized in FIG. 2 by flow opening 7), the increase in pressure in V1 will lead to a flow from V1 and primarily into V2. In that case, there will only be very little exchange of gases between the outside atmosphere and the system comprised by the patient's body and the device, leading to a very large decrease in $\dot{V}_A$. If, on the other hand, the resistance to flow into V2 is much larger than the flow resistance of flow opening 8, most of the total ventilation of the patient will flow out into the atmosphere, leading to a very small decrease in $\dot{V}_A$.

If V1 and V2 are in the form of for example a thin-walled polyethylene rebreathing air chamber with a volume larger than the Vital Capacity (i.e. the maximal expirable volume after a maximal inspiration) of the user, the flow of air into V2 will lead primarily to A) an expansion of the rebreathing air chamber and B) a flow of expired air into the atmosphere through flow opening 8, and only secondarily to an increase of pressure in V2 (i.e. the rebreathing air chamber functions as an almost perfect air reservoir and pressure buffer). Consequently, with such a configuration only a negligible back-pressure builds up in V1 when the device is in use, which is desirable.

Comparing with equation (2), the following formula is derived for calculating $\dot{V}_A$ for such an expandable-dead-space device:

$$\dot{V}_A = f_R * (\dot{V}_T - \dot{V}_{D,A} - \dot{V}_{D,D}) * (1 - RBR) \qquad (3),$$

where $f_R$ is the breathing rate, $V_T$ is the tidal volume (the volume of one breath), $V_{D,A}$ is the anatomical dead space, $V_{D,D}$ is the dead space of the device's mouth piece, and RBR is the Rebreathing Ratio.

In an alternative formulation the RBR may be defined as the volume entering the rebreathing air chamber ($\dot{V}_7$, i.e. the volume flow through opening 7) divided by the total volume of exhaled gas ($\dot{V}_6$, i.e. the volume flow through opening 6):

$$RBR = \frac{\dot{V}_7}{\dot{V}_7 + \dot{V}_8} = \frac{\dot{V}_7}{\dot{V}_6} = \frac{\dot{V}_7}{\dot{V}_T} \qquad (4a)$$

Figure 3:
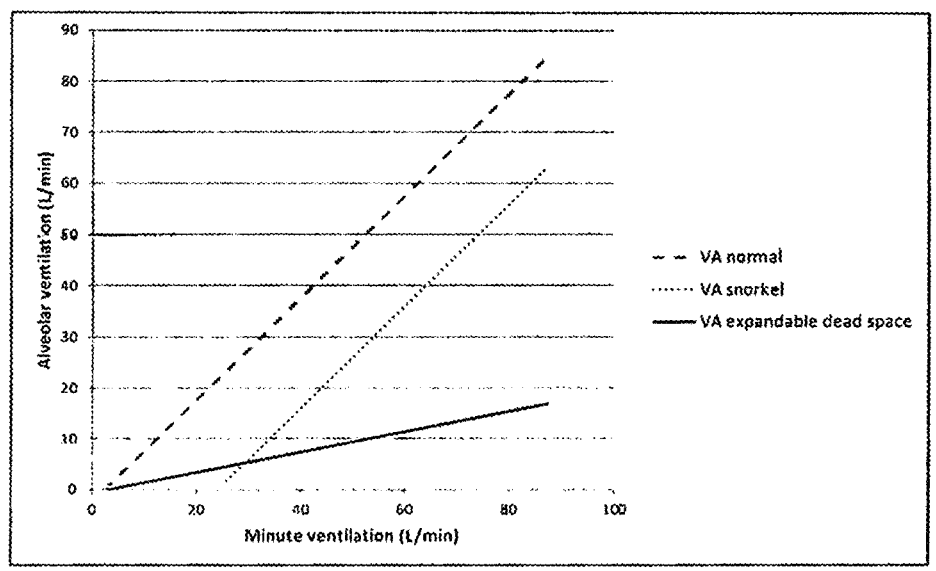
FIG. 3 illustrates $\dot{V}_A$ (delivery of fresh air to the alveolar space of the lungs) as a function of $\dot{V}_E$ (total ventilation pr. minute).

FIG. 3 illustrates $\dot{V}_A$ as a function of $\dot{V}_E$ ($\dot{V}_E$=total ventilation pr. minute, including dead space ventilation) at baseline (green, dashed line), while breathing through a snorkel-type rigid dead space of 1.5 liters (red, dotted line) and while breathing through the breathing device, expandable dead space with a RBR of 0.8 (blue solid line), the respiratory frequency being assumed constant in all situations and ventilation rates.

Irrespective of the snorkel volume and the RBR value, equation (3) shows that the $\dot{V}_A/\dot{V}_E$ will always be less steep for the breathing device as opposed to snorkel-type rebreathing, for the reason that, with the breathing device, the rebreathed volume scales to the tidal volume, so that even if the patient has a very strong ventilatory reaction to the elevated $F_{ICO2}$, he or she will be less able to reduce the rise in $P_{aCO2}$ than with a snorkel-type device.

FIG. 3 also illustrates that the breathing device generally has a lower $\dot{V}_E$ for a given $\dot{V}_A$ compared to a snorkel-type device.

RBR is not constant but varies over each inbreath. Apart from being time-dependent, the magnitude of RBR depends, among other factors on:

the compliance C of the rebreathing chamber (this is to a large extent a function of the chamber wall material and thickness, as well as the volume of the chamber)

the combined conductance G of the holes in the wall of the rebreathing chamber and/or mouthpiece (in preferred embodiments of the device, G can be adjusted, for example by use of a valve or slider controlling the size and/or number of holes in the wall of the rebreathing chamber or mouthpiece)

the lowest volume of the rebreathing chamber reached during the breathing cycle (reached at End-Inspiration, so denoted $V_{RC,EI}$)

the tidal volume the timing and duration of in- and expiration (See derivation of RBR from determining factors, below)

It is desirable to design the device with a C value and a range of adjustable G values, such that a given user (having individual values of tidal volume, breathing rhythm and $V_{RC,EI}$ when using the device) will obtain an RBR between 0.5 and 0.9, such as between 0.5 and 0.95.

RBR, Derivation from G, C and Other Determining Factors

Glossary for this section: (in order of mention)

$V_{RC,I}(t)$ = Volume of the rebreathing chamber (RC) during inspiration (time-dependent)

$V_{RC,EE}$ = Volume of the RC at end of expiration $\frac{dV_{RC,I}}{dt}$ = RC volume change rate, during inspiration $\frac{dV_I}{dt}$ = Flow rate of air inspired during inspiration (i.e. flow out of the RC)

$\frac{dV_{atm,I}}{dt}$ = Flow rate of air into the RC from the atmosphere, during inspiration t = time $\Delta P$ = pressure difference between the inside of the RC and the atmosphere $\frac{dV_{LA,RC,I}}{dt}$ = change rate of the volume of previously expired lung air in the RC, during inspiration $F_{LA,RC,I}(t)$ = Fraction of the RC volume comprised of previously expired lung air during the inspiration (time-dependent)

$V_{LA,RC,I}(t)$ = Volume of previously expired lung air in the RC, during inspiration (time-dependent), i.e. a subvolume of the total RC volume $V_{RC,EI}$ = Volume of the RC at end of inspiration $K_I$ = integration constant pertaining to the inspiratory phase $V_T$ = tidal volume $V_{RC,E}(t)$ = Volume of the rebreathing chamber (RC) during expiration (time-dependent)

$\frac{dV_{RC,E}}{dt}$ = RC volume change rate, during expiration $\frac{dV_E}{dt}$ = Flow rate of air expired during expiration (i.e. flow out of the RC)

$\frac{dV_{atm,E}}{dt}$ = Flow rate of air out of the RC into the atmosphere, during expiration $\frac{dV_{LA,RC,E}}{dt}$ = change rate of the volume of previously expired lung air in the RC, during expiration $F_{LA,RC,E}(t)$ = Fraction of the RC volume comprised of lung air during the expiration (time-dependent)

$V_{LA,RC,E}(t)$ = Volume of previously expired lung air in the RC, during expiration (time-dependent), i.e. a subvolume of the total RC volume $K_E$ = integration constant pertaining to the expiratory phase EI = end of inspiration time point EE = end of expiration time point = the ratio between $V_{LA,RC}$ at the end of inspiration and $V_{LA,RC}$ at the beginning of inspiration The interdependency between RBR and its determining factors can be derived as follows, assuming:

perfect mixing in the RC (which due to considerably turbulence can be assumed in RCs with volumes within an order of magnitude of the tidal volume of the user)

negligible gas density differences throughout the system (i.e. less than 2% variation in densities, as will be the case in normal breathing conditions where pressure differences compared to atmospheric pressure very seldom exceed 0.5 kPa=0.5% of atmospheric pressure)

steady state, cyclic breathing, i.e. no significant changes in tidal volume etc. between breaths During inspiration, the volume of the RC starts out at the End-Expiratory volume and changes as the user inspires air from the RC and new atmospheric air flows in from outside the following, yielding that:

$$V_{RC,I(t)} = V_{RC,EE} + \frac{dV_{RC,I}}{dt} \cdot t = V_{RC,EE} + \left(-\frac{dV_I}{dt} + \frac{dV_{atm,I}}{dt}\right) \cdot t \quad (4)$$

The flow into the RC from the atmosphere depends on the conductance and the pressure difference across the RC wall:

$$\frac{dV_{atm}}{dt} = \Delta P \cdot G, \quad (5)$$

and the change in RC volume in depends on the RC's compliance and the pressure difference across the RC wall:

$$\frac{dV_{RC}}{dt} = \Delta P \cdot C \quad (6)$$

The rate of change of lung air in the RC is:

$$\frac{dV_{LA,RC,I}}{dt} = \frac{-dV_I}{dt} \cdot F_{LA,RC,I}(t) = \frac{-dV_I}{dt} \cdot \frac{V_{LA,RC,I}(t)}{V_{RC,I}(t)} \quad (7)$$

i.e. the higher the fraction of lung air in the RC, the larger the volume of lung air removed from the RC with the air flow inspired from the RC by the user. The fraction of lung air in the RC changes over the course of the inspiration since it is a function of the volume of lung air in the RC and the volume of the RC.

By inserting eq. 5 and 6 into eq. 4 and then inserting in eq. 7, it follows that:

$$\frac{dV_{LA,RC,I}}{dt} + \frac{\Delta P \cdot (G-C)}{V_{RC,EE} + \Delta P \cdot C \cdot t} \cdot V_{LA,RC,I}(t) = 0 \quad (8)$$

Which is an ordinary differential equation with the solution:

$$V_{LA,RC,I}(t) = K_I (\Delta P \cdot C \cdot t + V_{RC,EE})^{(1-G/C)},$$

which using that ($V_{RC,EE} = V_{RC,EI} + V_T$) can be rewritten as:

$$V_{LA,RC,I}(t) = K_I (\Delta P \cdot C \cdot t + V_{RC,EI})^{(1-G/C)}. \quad (9)$$

RBR is by definition equal to the fraction of inspired lung air in total inspired air at any given time ($F_{LA,RC,I}$). In combination with eqs. 4-9 this yields that:

$$RBR = F_{LA,RC,I}(t) = \frac{V_{LA,RC,I}(t)}{V_{RC,I}(t)} = K_I \cdot (V_{RC,EE} + \Delta P \cdot C \cdot t)^{-G/C} \quad (10)$$

$$\Leftrightarrow RBR = K_I \cdot (V_{RC,EI} + V_T + \Delta P \cdot C \cdot t)^{-G/C}$$

For the expiratory phase, lung air is both entering and leaving the RC (entering from the user, and leaving to the atmosphere due to the overpressure inside the RC during expiration). Because flow directions are reversed compared to eq. 7, the following applies to the volume of the RC during expiration:

$$V_{RC,E(t)} = V_{RC,EI} + \frac{dV_{RC,E}}{dt} \cdot t = V_{RC,EE} + \left(\frac{dV_E}{dt} - \frac{dV_{atm,E}}{dt}\right) \cdot t \quad (11)$$

Using analogous arguments as for the inspiratory phase, it follows that:

$$\frac{dV_{LA,RC,E}}{dt} = \quad (12)$$

$$\frac{dV_E}{dt} - \frac{dV_{atm,E}}{dt} \cdot F_{LA,RC,E}(t) = \frac{dV_E}{dt} - \frac{dV_{atm,E}}{dt} \cdot \frac{V_{LA,RC,E}(t)}{V_{RC,E}(t)}$$

$$\Leftrightarrow \frac{dV_{LA,RC,E}}{dt} = \Delta P \cdot (G+C) - \frac{\Delta P \cdot G}{V_{RC,EI} + \Delta P \cdot C \cdot t} \cdot V_{LA,RC,E}(t) \quad (13)$$

Which is an ordinary differential equation, with the solution:

$$V_{LA,RC,E}(t) = K_E \cdot (\Delta P \cdot C \cdot t + V_{RC,EI})^{(G/C)} + V_{RC,EI} + \Delta P \cdot C \cdot t \quad (14)$$

The integration constants $K_I$ and $K_E$ in eqs. 9 and 14 influence the values of $V_{LA,RC}$ at the beginning and end of the breathing phases. They are determined by the reasonable assumption of a cyclic steady-state, i.e. that the breathing cycle returns all values to their original value from the beginning of one breathing cycle to the beginning of the next. Coupled with an assumption of negligible diffusion (as opposed to the bulk flow taking place during in—and expiration) between the inside of the RC and the atmosphere, it is therefore a requirement that:

$$V_{LA,RC,I}(t=EI) = V_{LA,RC,E}(t=0) \quad (15)$$

$$V_{LA,RC,E}(t=EE) = V_{LA,RC,I}(t=0) \quad (16)$$

Eqs. 15 and 16 can be expanded using equation 9 and 14, yielding:

$$K_I (\Delta P \cdot C \cdot \Delta t_I + V_{RC,EI} + V_T)^{(1-G/C)} = K_E \cdot V_{RC,EI}^{-G/C} + V_{RC,EI} \quad (17)$$

and $$K_E \cdot (\Delta P \cdot C \cdot \Delta t_E + V_{RC,EI})^{(G/C)} + V_{RC,EI} + \Delta P \cdot C \cdot \Delta t_E = K_I (V_{RC,EI} + V_T)^{(1-G/C)} \quad (18)$$

By dividing Eq. 17 by Eq. 18, $K_I$ is eliminated and $K_E$ can be isolated:

$$V_{RC,EI} - V_{RC,EI} * \frac{(\Delta P \cdot C \cdot \Delta t_I + V_{RC,EI} + V_T)^{(1-G/C)}}{(V_{RC,EI} + V_T)^{(1-G/C)}} - \quad (19)$$

$$K_E = \frac{\Delta P \cdot C \cdot \Delta t_E * \frac{(\Delta P \cdot C \cdot \Delta t_I + V_{RC,EI} + V_T)^{(1-G/C)}}{(V_{RC,EI} + V_T)^{(1-G/C)}}}{\left((\Delta P \cdot C \cdot \Delta t_E + V_{RC,EI})^{(-G/C)} * \frac{(\Delta P \cdot C \cdot \Delta t_I + V_{RC,EI} + V_T)^{(1-G/C)}}{(V_{RC,EI} + V_T)^{(1-G/C)}} - V_{RC,EI}^{-G/C}\right)}$$

The expression $$\frac{(\Delta P \cdot C \cdot \Delta t_I + V_{RC,EI} + V_T)^{(1-G/C)}}{(V_{RC,EI} + V_T)^{(1-G/C)}}$$

appearing three times in Eq. 19 is the ratio between $V_{LA,RC}$ at the end of inspiration and $V_{LA,RC}$ at the beginning of inspiration, and will for simplicity's sake be denoted RI, yielding a simpler expression for $K_E$, which can be inserted in Eq. 17 to yield an expression for $K_I$, which can again be inserted in Eq. 10 to yield the end equation for RBR as a function of the determining factors:

$$RBR = \left(\frac{V_{RC,EI}(1-R_I) - \Delta P \cdot C \cdot \Delta t_E \cdot R_I}{R_I \cdot (\Delta P \cdot C \cdot \Delta t_E + V_{RC,EI})^{(-G/C)} - V_{RC,EI}^{-G/C}} \times \right. \quad (20)$$

$$\frac{V_{RC,EI}^{-G/C}}{(\Delta P \cdot C \cdot \Delta t_I + V_{RC,EI} + V_T)^{(1-G/C)}} +$$

$$\left.\frac{V_{RC,EI}}{(\Delta P \cdot C \cdot \Delta t_I + V_{RC,EI} + V_T)^{(1-G/C)}}\right) \times$$

$$(V_{RC,EI} + V_T + \Delta P \cdot C \cdot t)^{-G/C}$$

$$R_I = \frac{(\Delta P \cdot C \cdot \Delta t_I + V_{RC,EI} + V_T)^{(1-G/C)}}{(V_{RC,EI} + V_T)^{(1-G/C)}} \quad (21)$$

Equations 20 and 21 constitute the mathematical/physical underpinnings of any partial rebreathing device and can be used for guiding the design and experimentation process when sizing G and C so as to produce desired device RBR ratios.

Measuring G and C

The determination of the conductance G of RC wall section(s) can be determined by standard air permeability tests for filter materials (e.g. by measuring the induced flow through the material at a pre-specified pressure difference across the material).

The determination of the RC's compliance C could be done by experiments with the rebreathing air chamber. By changing the geometry and/or material of the second wall section, various values of C are obtained.

The first type of experiments could be physiological, i.e., measuring inhaled $CO_2$ percent, minute ventilation and total $CO_2$ production (can be done using ergospirometrical equipment) and the arterial $CO_2$ of a patient.

Another type of experiment would include measuring the pressure at various volume change rates (dV/dt) of the rebreathing air chamber when all holes in the RC chambers are closed off. One way of doing the experiment would be to take a large air syringe and empty it into the mouthpiece, for example in 1, 2, 3 and 4 seconds respectively, and measure the overpressure ($\Delta P = P_1 - P_{atm}$) at the distal end of the mouthpiece, this being the pressure that expands the rebreathing air chamber. Because the flow rates in this experiment are predetermined (and therefore known) and because the flow rates roughly correspond to the volume expansion rates (dV/dt) of the rebreathing air chamber (since all holes in the RC wall are closed), C can now be calculated as the volume expansion rate divided by the extending pressure=$(dV_{RC}/dt)/\Delta P$.

Impact of RBR on $P_{aCO2}$

Combining equations 1 to 3 gives the following approximate expression of $P_{aCO2}$ as a function of RBR and the device-specific values of $V_{D,D}$:

$$P_{aCO2} = \frac{0.863 * V_{CO2}}{f_R * (V_T - V_{D,A} - V_{D,D}) * (1 - RBR)} = \tag{22}$$

It can be seen from equation 22 that RBR has a large impact on $P_{aCO2}$. In addition, it is necessary to take into account the increase in minute ventilation resulting from increasing the arterial $P_{aCO2}$ level. $V_E$ increases linearly when elevating $P_{aCO2}$ above normal (though the slope varies from person to person), i.e. the expression is of the form:

$$\dot{V}_E = f_R * V_T = a*(P_{aCO2} - P_{aCO2,baseline}) + \dot{V}_{E,baseline} \tag{23}$$

By combining equations 22 and 23, a final expression is achieved:

$$P_{aCO2} = \frac{0.863 * V_{CO2}}{f_R * \left[\left(\frac{a*(P_{aCO2} - P_{aCO2,baseline}) + \dot{V}_{E,baseline}}{f_R}\right) - V_{D,A} - V_{D,D}\right] * (1 - RBR)} \tag{24}$$

$\Leftrightarrow$ $$RBR = 1 - \left(\frac{0.863 * V_{CO2}}{f_R * \left[\left(\frac{a*(P_{aCO2} - P_{aCO2,baseline}) + \dot{V}_{E,baseline}}{f_R}\right) - V_{D,A} - V_{D,D}\right] * P_{aCO2}}\right) \tag{25}$$

From this expression, it is possible to calculate curves of $P_{aCO2}$ as a function of RBR of the device, for patients with either a normal ventilatory response to inspired $CO_2$ (a=2.4) as well as patients with a low response (a=1.2) and a high response (a=3.6). Without being bound by theory, it has been shown that individuals with a high ventilatory response to $CO_2$ also have a low baseline $P_{aCO2}$, and individuals with a low ventilatory response to $CO_2$ have a high baseline $P_{aCO2}$, which provides more knowledge about the input parameters for equation (9) and makes it possible to plot the aforementioned curves.

Figure 4:
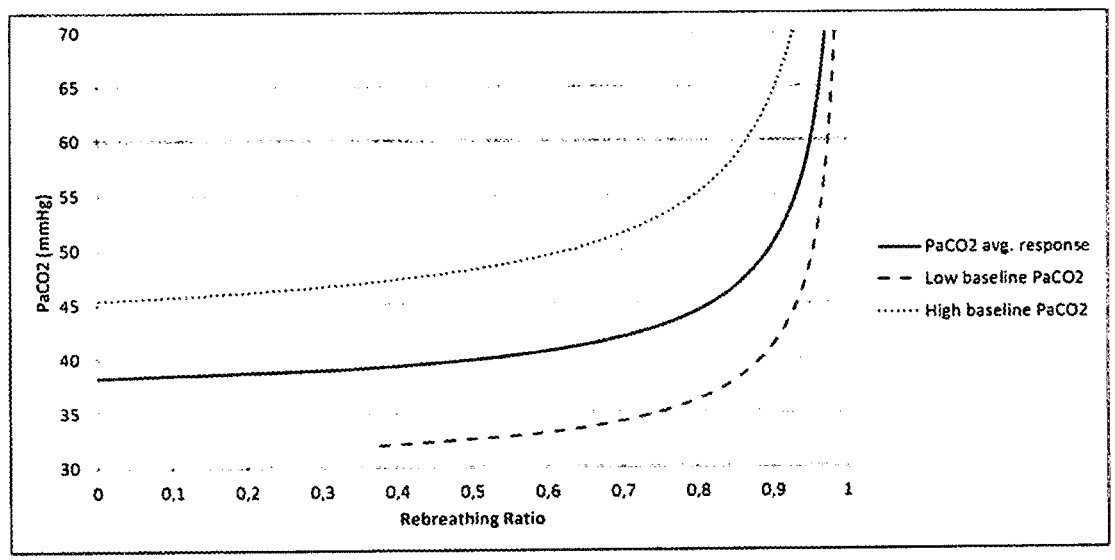
FIG. 4 illustrates $P_{aCO2}$ (arterial partial pressure of $CO_2$) as a function of RBR (rebreathing ratio).

The calculations illustrated in FIG. 4 gives the following results:

In order to increase $P_{aCO2}$ by 20% from baseline (20% being the average desired value from a clinical viewpoint), the following RBR values are needed:

High responder patient (a=3.6), low baseline $P_{aCO2}$ (=31 mmHg): RBR=0.82. Inspired $CO_2$ fraction ($F_{ICO2}$) with this RBR at steady state=4.0%

Average responder (a=2.4), normal baseline $P_{aCO2}$ (=38 mmHg): RBR=0.83. $F_{ICO2}$=5.0% at steady state.

Low responder (a=1.2), high baseline $P_{aCO2}$ (=45 mmHg): RBR=0.77. $F_{ICO2}$=5.5% at steady state.

If only a 10% increase in $P_{aCO2}$ is desired, the RBR values for high, average and low responders are, 0.68, 0.69 and 0.60 respectively, with $F_{ICO2}$ values of 3.0%, 3.8% and 3.9% at steady state.

As indicated from the $F_{ICO2}$ values above, an equation can be derived, linking the inspired $CO_2$ fraction to the RBR, thus describing how the functionality of the device (its inspired $CO_2$ fraction) depends on RBR of the device:

$$F_{ICO2} = \frac{F_{ACO2} * RBR * (V_T - V_{D,A} - V_{D,D})}{V_T - RBR * (V_{D,A} + V_{D,D})} \sim \frac{P_{aCO2}}{P_{atm}} * \tag{26}$$

$$\frac{RBR * \left[\left(\frac{a*(P_{aCO2} - P_{aCO2,baseline}) + \dot{V}_{E,baseline}}{f_R}\right) - V_{D,A} - V_{D,D}\right]}{\left(\frac{a*(P_{aCO2} - P_{aCO2,baseline}) + \dot{V}_{E,baseline}}{f_R}\right) - RBR * (V_{D,A} - V_{D,D})}$$

Because of the variability of the ventilatory response to $CO_2$, the increase in $P_{aCO2}$ with a given RBR will vary between individuals, as shown above. In order to adjust the $P_{aCO2}$ increase to the desired level, some embodiments of this type of breathing device could be equipped with adjustable bypass-valves providing an adjustable flow connection between the inside of the breathing device and the atmosphere (for example situated in the wall of the mouthpiece). RBR of the breathing device would thus be adjusted by opening the valve or otherwise increasing the conductance of the flow connection between the air volume inside the breathing device and the source of fresh gas (be it the outside atmosphere or another gas source).

Alternatively, different RBR values can be provided by changing between rebreathing chambers with different relative areas of permeable and non-permeable wall sections and/or different hole sizes and/or hole spacing. Such geometrical differences will lead to different values of G, C and RBR, thereby allowing the $P_{aCO2}$ increase elicited by the device to be varied.

Alternative formulation In a simplified mathematical model represented by FIG. 2, the flows $\dot{V}_7$ and $\dot{V}_8$ can be calculated as:

$$\dot{V}_7 = \frac{P_{(V1)} - P_{AT}}{R_7} = \Delta P * G_7 = \Delta P * G_{expand} \tag{5a}$$

$$\dot{V}_8 = \frac{P_{(V1)} - P_{AT}}{R_8} = \Delta P * G_8 = \Delta P * G_{out} \tag{6a}$$

($P_{(V1)}$=total pressure in V1, $P_{AT}$=total atmospheric pressure, $R_7=R_{expand}$=flow resistance of second wall section (the resistance to expansion of the rebreathing air chamber which must be overcome by a pressure difference), $G_7=G_{expand}$=conductance (inverse flow resistance) of second wall section, $R_8=R_{out}$=flow resistance of first wall section, $G_8=G_{out}$=conductance of first wall section.)

RBR is defined as the volume of gas entering the rebreathing air chamber, divided by the total volume of exhaled gas, or expressed in the terms of conductances: RBR=$G_{expand}/(G_{expand}+G_{out})$, RBR having a value between 0.5 and 0.9.

The determination of the flow resistance $R_{out}$ of the first wall section (having the conductance $G_{out}$), can be done mathematically, by means of the geometry and material of the first wall section. Preferably, $R_{out}$ of the first wall section can be determined by standard air permeability tests for filter materials (e.g. by measuring the induced flow through the material at a pre-specified pressure difference across the material).

The determination of $G_{expand}$ could be done by experiments with the rebreathing air chamber. By changing the geometry and/or material of the second wall section, various values of $G_{expand}$ are obtained.

The first type of experiments could be physiological, i.e., measuring inhaled $CO_2$ percent, minute ventilation and total $CO_2$ production (can be done using ergospirometrical equipment) and the arterial $CO_2$ of a patient. From equation (7) it is possible to deduce $G_{expand}$ when the above parameters is measured and $G_{out}$ is known.

Another type of experiment would include measuring the pressure at various volume change rates (dV/dt) of the rebreathing air chamber. One way of doing this could be to take a large air syringe and empty it into the mouthpiece, for example in 1, 2, 3 and 4 seconds, and measure the overpressure ($\Delta P = P_1 - P_{atm}$) at the distal end of the mouthpiece, this being the pressure that expands the rebreathing air chamber. Because the flow rates in this experiment are predetermined (and therefore known) and because the flow rates roughly correspond to the volume expansion rates (dV/dt) of the rebreathing air chamber, $G_{expand}$ can now be calculated with equation (5), which states that $G_{expand}$= (volume expansion rate)/(extending pressure)=(dV/dt)/($P_1 - P_{atm}$).

Combining equations 1, 3, 4, 5 and 6 gives the following approximate expression of $P_{aCO2}$ as a function of the device-specific values of $V_{D,D}$, $G_{expand}$ and $G_{out}$:

$$P_{aCO2} = \frac{0.863 * V_{CO2}}{f_R * (V_T - V_{D,A} - V_{D,D}) * \left(1 - \frac{G_{expand}}{G_{out} + G_{expand}}\right)} \quad (7a)$$

It can be seen from equation (7) that the dimensioning of $V_{D,D}$, $G_{expand}$ and $G_{out}$, has a large impact on $P_{aCO2}$. In addition, it is necessary to take into account the increase in minute ventilation resulting from increasing the arterial $P_{aCO2}$ level. $V_E$ increases linearly when elevating $P_{aCO2}$ above normal (though the slope varies from person to person), i.e. the expression is of the form:

$$\dot{V}_E = f_R * V_T = a * (P_{aCO2} - P_{aCO2,baseline}) + \dot{V}_{E,baseline} \quad (8a)$$

By combining equations (7) and (8), a final expression is achieved:

$$P_{aCO2} = \frac{0.863 * V_{CO2}}{f_R * \left[\left(\frac{a*(P_{aCO2} - P_{aCO2,baseline}) + \dot{V}_{E,baseline}}{f_R}\right) - V_{D,A} - V_{D,D}\right] * (1 - RBR)} \quad (9a)$$

$$RBR = 1 - \left(\frac{0.863 * V_{CO2}}{f_R * \left[\left(\frac{a*(P_{aCO2} - P_{aCO2,baseline}) + \dot{V}_{E,baseline}}{f_R}\right) - V_{D,A} - V_{D,D}\right] * P_{aCO2}}\right)$$

From this expression, it is possible to calculate curves of $P_{aCO2}$ as a function of RBR of the device, for patients with either a normal ventilatory response to inspired $CO_2$ (a=2.4) as well as patients with a low response (a=1.2) and a high response (a=3.6). Without being bound by theory, it has been shown that individuals with a high ventilatory response to $CO_2$ also have a low baseline $P_{aCO2}$, and individuals with a low ventilatory response to $CO_2$ also have a high baseline $P_{aCO2}$, which provides more knowledge about the input parameters for equation (9) and makes it possible to plot the aforementioned curves.

The calculations illustrated in FIG. 4 gives the following results:

In order to increase $P_{aCO2}$ by 20% from baseline (20% being the average desired value from a clinical viewpoint), the following RBR values are needed:

High responder patient (a=3.6), low baseline $P_{aCO2}$ (=31 mmHg): RBR=0.82. Inspired $CO_2$ fraction ($F_{ICO2}$) with this RBR at steady state=4.0%

Average responder (a=2.4), normal baseline $P_{aCO2}$ (=38 mmHg): RBR=0.83. $F_{ICO2}$=5.0% at steady state.

Low responder (a=1.2), high baseline $P_{aCO2}$ (=45 mmHg): RBR=0.77. $F_{ICO2}$=5.5% at steady state.

If only a 10% increase in $P_{aCO2}$ is desired, the RBR values for high, average and low responders are, 0.68, 0.69 and 0.60 respectively, with $F_{ICO2}$ values of 3.0%, 3.8% and 3.9% at steady state.

As indicated from the $F_{ICO2}$ values above, an equation can be derived, linking the inspired $CO_2$ fraction to the RBR, thus describing how the functionality of the device (its inspired $CO_2$ fraction) depends on its design (the values of conductance's $G_{expand}$ and $G_{out}$ yielding a certain RBR):

$$F_{ICO2} = \frac{F_{ACO2} * RBR * (V_T - V_{D,A} - V_{D,D})}{V_T - RBR*(V_{D,A} + V_{D,D})} \sim \frac{P_{aCO2}}{P_{atm}} *$$

$$\frac{RBR * \left[\left(\frac{a*(P_{aCO2} - P_{aCO2,baseline}) + \dot{V}_{E,baseline}}{f_R}\right) - V_{D,A} - V_{D,D}\right]}{\left(\frac{a*(P_{aCO2} - P_{aCO2,baseline}) + \dot{V}_{E,baseline}}{f_R}\right) - RBR*(V_{D,A} - V_{D,D})}$$

Because of the variability of the ventilatory response to $CO_2$, the increase in $P_{aCO2}$ with a given RBR will vary between individuals, as shown above. In order to adjust the $P_{aCO2}$ increase to the desired level, some embodiments of this type of breathing device could be equipped with adjustable bypass-valves providing an adjustable flow connection between the inside of the breathing device and the atmosphere (for example situated in the wall of the mouthpiece). RBR of the breathing device would thus be adjusted by opening the valve or otherwise increasing the conductance of the flow connection between the air volume inside the breathing device and the source of fresh gas (be it the outside atmosphere or another gas source).

Alternatively, different RBR values can be provided by changing between rebreathing chambers with different relative areas of permeable and non-permeable wall sections and/or different hole sizes and/or hole spacing. Such geometrical differences will lead to different values of $G_{expand}$, $G_{out}$ and RBR, thereby allowing the $P_{aCO2}$ increase elicited by the device to be varied.

Alternative Way to Measure the Functionality of the Breathing Device

Figure 17:
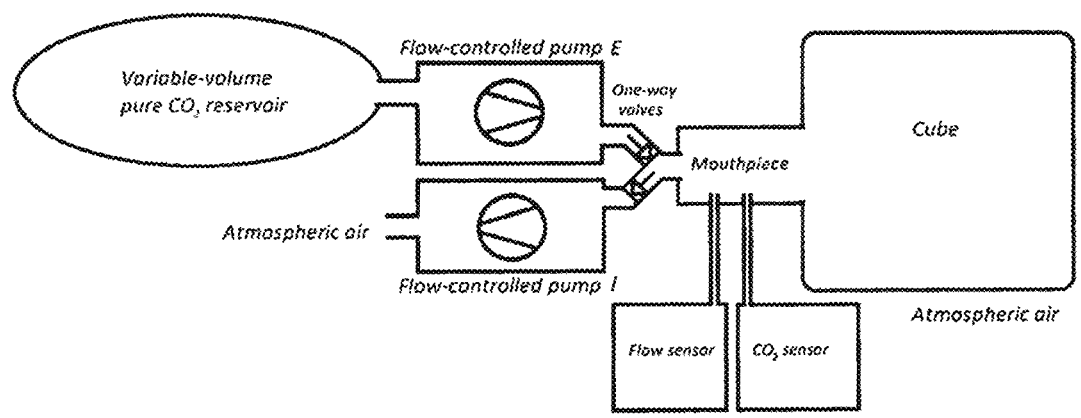
FIG. 17 illustrates an experimental set-up useable for measuring the RBR (rebreathing air ratio).

Another way to measure the functionality of the breathing device could be to measure the RBR with the experimental set-u in FIG. 17.

A controlled amount of pure $CO_2$ is pumped into the rebreathing air chamber ("cube" in the figure above) through the mouthpiece and back again out through the mouthpiece, as the $CO_2$ level and flow is measured by sensors. The sensor measurements of $CO_2$ and flow should be synchronized and have a sampling rate, corresponding to the time from the start-inhalation to end-inhalation, divided into at least 100 measuring points. The $CO_2$ acts as a tracer, since all the $CO_2$ which is measured in the air inhaled is known to originate from the exhaled air.

The RBR can then be calculated with the following equation:

$$RBR = \frac{V_{inspired\_from\_cube}}{V_{inspired\_total}} = \frac{V_{CO2\_inspired}}{V_{inspired\_total}} = \frac{\sum_{t=t\_start\_insp}^{t=t\_end\_insp} \dot{V}(t) \times F_{CO2}(t)}{\sum_{t=t\_start\_insp}^{t=t\_end\_insp} \dot{V}(t)} \quad (27)$$

where $V_{inspired\_from\_cube}$ is the volume of the inhaled air (inhaled air=air pumped through the pump L) constituted by the previously exhaled air.

$V_{inspired\_total}$ is the total volume of inspired air $V_{CO2\_inspired}$ is the total volume of inspired CO2 t is the time t_start_insp is the time when the inhalation via pump I begins t_end_insp is the time when the inhalation via pump I ends V_dot(t) is the volumetric flowrate at time t $F_{CO2}(t)$ is the fraction of CO2 (0=0% CO2, 1=100% CO2) at the time t. Without being bound by theory, by this experiment it will be possible to measure RBR for breathing devices with different G and C values, and also examine how RBR is affected by other factors identified in the derivation of RBR above (among them the timing and length of the various phases of breathing-cycle (inhalation, I-E pause, exhale, E-I pause), the lowest volume of the rebreathing chamber reached during the breathing cycle and the tidal volume).

It is not compulsory to use pure CO2 in the exhaled air, but it makes the calculation of RBR simpler, since Eq. 27 can be used.

Reference is made to FIGS. 16a-c schematically illustrating the step of unfolding a rebreathing air-chamber connector 26 according to an aspect of the invention. In FIG. 16a, the connector 16 is illustrated in a folded configuration and in the FIGS. 16b and c the connector 16 is illustrated in its unfolded configuration. FIG. 16c illustrates the process of unfolded the rebreathing air-chamber 15 by pulling in the strip labelled X (#37).

As illustrated in the FIGS. 16a-c, the rebreathing air-chamber-connecter 26, is foldable by comprising a number of parallel extending folding lines 32 arranged in said connector 26 to allow the air-breathing connector 26 to be folded into a configuration defining a void 33, preferably being cuboid as illustrated in FIG. 16a. The dimension of the breathing air-chamber connector 26 is preferably selected so that when in folded configuration, at least part of the rebreathing air-chamber 15 is accommodated inside the void 33 as illustrated in FIG. 16a. It is noted that the rebreathing air-chamber is folded when accommodated inside the void. The folding lines 32 may preferably be in the form of locally thinner material thickness defining a section that bend more easily than the rest of the connector 26 so that theses folding lines 32 each form a hinge mechanism.

As illustrated in FIG. 16b, the rebreathing air-chamber-connector has a slider 24 providing an opening into said breathing air chamber 15 when said slider 24 is moved to one side (and the rebreathing air chamber is unfolded as illustrated in FIGS. 16b and c). As illustrated in FIGS. 16b and 16c, the slider uncovers an opening and since the position of the slider can be varied by a used, the size of the opening can be adjusted by the user, thus the slider (24) can be seen as being configured for adjusting the flow of air into said rebreathing air chamber 15 by uncover or cover one or more through going opening 30. As indicated in FIGS. 16b and 16c, the slider may be formed as roll front.

The rebreathing air-chamber-connector 26 as illustrated in FIGS. 16a-c further comprising through one or more through going openings 27—preferably as disclosed in connection with other embodiments of the invention—being non-adjustable in size, and allowing fluid communication in and/or out of the rebreathing air chamber with the surrounding atmosphere. It is noted that in some embodiments, one of slider mechanism 24 or through going opening 27 may be left out. In still further embodiments, none of the slider mechanism and through going openings 27 are provided in the connector 26.

As also illustrated in FIGS. 16a-c, the rebreathing air-chamber connector 26 comprising an elongate unfold element 34 (typically in the form of a strip) extending slide-able in a direction being perpendicular to the folding lines along a surface of said connector 26. The unfold element 34 is fixed at one end 34a to the connector 26—within the scope of fixed at one end is considered also the situation where the unfold element 34 is made integral with the connector 26. Thus, by pulling (typically by a user) in the unfold element 34 and an end being opposite to the fixed end 34a, an unfolding the rebreathing air-chamber-connector 26 from its folded configuration. This is illustrated in FIGS. 16a and b by the bold arrow in FIG. 16 indicating the by pulling in the direction of the bold arrow, the connector 26 unfold from its folded configuration in FIG. 16a to its unfolded configuration shown in FIG. 16b.

To maintain the elongate unfold element 34 in its desired position relatively to the connector 26, the rebreathing air-chamber connector 26 comprising guide elements 35 to maintain the elongate unfold element 34 in a guided position on said connector 26. These guide elements 35 are designed to allow a pulling action in the elongate unfold element 34 while preventing the elongate unfold element 34 to move sideward.

The elongate unfold element 34 and/or the rebreathing air-chamber connector 26 typically comprising a latch configured for latching the elongate unfold element's position when the said rebreathing air-chamber connector 26 is in its unfolded configuration. This latch is not illustrated in FIG. 16a-c (but indicated by "Click" in these figures). The latch is typically made as is know from fastening strip and comprises protrusion provided either on the elongate unfold element or on the connector, which protrusions engage with either protrusions or indentations on the other part.

As also illustrated in FIGS. 16a-c, the rebreathing air-chamber 15 comprises a strip 37, such as a pull-tab attached to a wall section of the rebreathing air-chamber allowing a user to expand the rebreathing air-chamber 15, preferably to unfold the rebreathing air-chamber from a folded configured, so as to make it easier for a user to exhale air into the rebreathing air-chamber.

In the following preferred embodiments and aspects of the invention are presented as a list of items:

Item 1. A breathing device (1), comprising
a mouthpiece (2) forming a breathing channel to form a connection between a first end and a second end of the mouthpiece (2), the first end being configured for a user breathing into the mouthpiece through a breathing opening (5),
an at least partly flexible rebreathing air chamber (15) attached to the second end of the mouthpiece, thereby being in fluid connection with the breathing channel, the rebreathing air chamber being formed by at least partly flexible wall section(s),
wherein
the at least partly flexible rebreathing chamber (15) having at a first wall (3, 10, 11, 16, 28) section being permeable to gas by one or more, such as a plurality of pores (36) and/or through going openings (27) provided in said wall section, and/or
the mouth piece (2) comprising one or more though going openings (19, 35) allowing fluid communication between the breathing channel and the surrounding atmosphere.

Item 2. A breathing device according to item 1, wherein said rebreathing air chamber (15) comprises
a number of through-going openings and/or pores in said at least partly flexible first wall section (3, 10, 11, 16, 28), said through going openings and/or pores provide a permeability to gas and having an overall flow conductance G, and
wherein the first wall section apart from said pores and/or through going openings is non-permeable to gas and deformable by a pressure differences across said first wall section, wherein said pressure difference is of a size provided by a user breathing into the rebreathing air chamber, giving the rebreathing chamber enclosed by said first wall section a substantial time-normalized compliance C, where C is determined as the volume expansion of the rebreathing chamber per second per pressure difference across said wall section,
wherein said rebreathing air chamber has a Rebreathing Ratio, preferably as defined herein, between 0.5 and 0.9, such as between 0.5 and 0.95.

Item 3. A breathing device according to item 1 or 2, wherein said rebreathing air chamber (3, 4) comprises
said first wall section (3) being permeable to gas and having a first conductance $G_{out}$, and
a second wall section (4) being impermeable to gas and having a second conductance $G_{expand}$
wherein the first and the second wall section are configured to provide a RBR defined as $RBR=G_{expand}/(G_{out}+G_{expand})$ between 0.5 and 0.9.

Item 4. A breathing device according any of the preceding items, wherein the rebreathing air chamber comprising a first wall section (3) being permeable to air and a second wall section being impermeable to air (4).

Item 5. A breathing device according to items 1-4, wherein said rebreathing air chamber (15) being formed by the flexible first wall section (3) and/or a flexible second wall section being permeable to gas by a plurality of pores and/or through going opening(s) provided in said wall section.

Item 6. A breathing device according to items 1-5, wherein said rebreathing chamber (15) being formed by the flexible wall section (11), is permeable to gas by a plurality of pores and/or through going openings arranged in lines or rows, distributed in the flexible wall section (11).

Item 7. A breathing device according to any of the preceding items, wherein the breathing device (1) further comprises an rebreathing air-chamber-connector (26), said connector (26) being configured
for connecting a facial mask or said mouthpiece (2) to said rebreathing air chamber (15), or
so that said connector (26) forms the mouth piece (2);
at least a part of said connector (28) forming at a least part of the first wall section and/or second wall section, said rebreathing-air-chamber-connector (26) allowing fluid communication in and/or out of the re-breathing air chamber (15) with a user's breath.

Item 8. A breathing device according to items 1-7, wherein the form of said rebreathing air chamber (15) is selected from the group comprising: cube, such as cuboid, sphere, such as spheroid, bag type, tetrahedron, such as substantially tetrahedron, square-based pyramid such as substantially pyramid, octahedron, such as substantially octahedron, hexagonal prism such as substantially prism, dodecahedron, such as substantially dodecahedron, cylinder, or cylindroid.

Item 9. A breathing device according to any of the preceding items, wherein said the form of rebreathing air chamber (15) is selected according to item 5, and the rebreathing air chamber comprising panels each defining a face of the rebreathing air chamber, one or more of said panels and/or at least a part of one of said panels form said first flexible wall section, and when dependant on item 3, at least one of said panels form at least a part of the second flexible wall section (18), said first wall section preferably comprising permeable sections or being permeable to gas by a plurality of pores and/or through going openings preferably arranged in lines or rows, distributed in the flexible first wall section.

Item 10. A breathing device according to item 9, wherein one or more of said panels comprise a first flexible wall section and/or second flexible wall section.

Item 11. A breathing device according to items 9-10, wherein said panels and/or wall sections has a thickness smaller than 4 mm, such as smaller than 2 mm, such as smaller than 1 mm.

Item 12. A breathing device according to item 7-11, wherein said rebreathing air chamber further comprises said breathing channel arranged in said rebreathing-air-chamber-connector (26), allowing fluid communication in and/or out of the rebreathing air chamber (15) with the user's mouth, during use.

Item 13. A breathing device according to items 7-12, wherein said breathing channel has at least one through going opening (19, 35), allowing fluid communication in and/or out of the breathing device with the surrounding atmosphere.

Item 14. A breathing device according to items 13, wherein one or more of said through going openings are re-closable and/or adjustable in size (34), e.g. by a valve mechanism (38).

Item 15. A breathing device according to items 13-14, wherein said through going openings (30) provided in the breathing channel are in the form of one or more opening, preferably covered by a slider (24), arranged between two parallel longitudinal wall sections (25), said slider providing an opening into said breathing channel (2) when said slider (24) is moved translatory between the two parallel longitudinal wall sections (25), said slider (24) configured for adjusting the flow of air into said rebreathing air chamber (15).

Item 16. A breathing device according to items 13-15, wherein said breathing channel further comprises two parallel longitudinal wall sections (20), protruding in a perpendicular direction to a breathing direction through the breathing channel, with a distance in between below 3 cm, such as below 2 cm preferably below 1 cm, configured for the user being preventing from blocking the through going openings with a finger, while holding said breathing device with the fingers, said through going openings (19) being arranged in between the two parallel longitudinal wall sections (20).

Item 17. A breathing device according to items—7-16, wherein the rebreathing air chamber comprises non-adjustable through going openings (27), arranged on the rebreathing-air-chamber-connector (26) allowing fluid communication in and/or out of the rebreathing air chamber with the surrounding atmosphere.

Item 18. A breathing device according to items 7-12, wherein said rebreathing air chamber-connector (26) further comprises a socket (29) configured for connecting the rebreathing air chamber to the mouth pieces while allowing fluid communication in and/or out of the rebreathing air chamber.

Item 19. A breathing device according to item 18, wherein one or more re-closable and/or adjustable openings, preferably comprises a slider (24) arranged between two parallel longitudinal wall sections (25), said slider arranged on said flexible wall section (18), said slider (24) providing an opening into said breathing air chamber (15) when said slider (24) is moved to one side between the two parallel longitudinal wall sections (25), said slider (24) being configured for adjusting the flow of air into said rebreathing air chamber (15).

Item 20. A breathing device according to item 18 or 19, wherein the socket (29) forms the mouth piece (2).

Item 21. A breathing device according to item 7-20 wherein said rebreathing-air-chamber connector (26) comprises non-adjustable through going openings (27) allowing fluid communication in and/or out of the rebreathing air chamber with the surrounding atmosphere, Item 22. A breathing device according to any of preceding items, wherein the through goings openings (19, 27) and/or the variable openings of the slider/valve(30) are configured for directing/angulating the outgoing fluid from the rebreathing air chamber away from the users face.

Item 23. A breathing device according to any of the preceding items, wherein the through going openings (19, 27) are in a round, rectangular and/or elliptical form.

Item 24. A breathing device according to any of the preceding items, wherein the hydraulic diameter of the through goings openings (19, 27) is $100*10^{-6}$ m to 2 cm, such as $100*10$ cm$^{-6}$ m to 3 cm per through going opening (19,27).

Item 25 A breathing device according to items 9-24, wherein the flexible walls sections (16, 18) are foldable such as by being pleated.

Item 26. A breathing device according to items 9-25, wherein said rebreathing air chamber (15) is assembled by a plurality of panels welded together to form a cube.

Item 27. A breathing device according to items 9-26, wherein said rebreathing air chamber (15) is assembled by four panels welded together to form a cube (17), each of the four panels being formed by two triangular wall elements arranged on opposite to each other sides of one square wall element.

Item 28. A breathing device according to any of the preceding items, wherein said plurality of pores and/or through going openings are equidistantly disturbed in the first flexible wall sections (10).

Item 29. A breathing device according to any of preceding items, wherein the hydraulic diameter of said pores and/or through going openings is smaller than 2 cm, such as smaller than $10^{-3}$ m, preferably equal to or smaller than $180*10^{-6}$ m.

Item 30. The breathing device (1) according to any of the preceding items, wherein said breathing opening (5) comprises a connection, such as a pipe, duct or other connection, preferably suitable for connecting the breathing device to a facial mask.

Item 31. The breathing device (1) according to any of the preceding items, wherein said first wall section (3) and/or second wall section (4), when present, are wholly or partially hydrophobic.

Item 32. The breathing device (1) according to any of the preceding items, wherein the rebreathing air chamber (15) has a volume between 1 and 16 liters, such as between 2 liters and 8 liters, preferably between 4 liters and 6 liters.

Item 33. The breathing device (1) according to any of the preceding items, wherein the first wall section (3) and/or second wall section are foldable such as pleated.

Item 34. The breathing device (1) according to any of the preceding items, wherein the rebreathing air chamber (15) is volumetrically sizeable by changing the geometry of the rebreathing air chamber and/or the permeability of the first wall section is sizeable, e.g. by uncovering pores and/or through openings e.g. by at least partially removing a strip attached to cover the pores and/or through going opening.

Item 35. The breathing device (1) according to any of the preceding items, wherein the breathing channel has a smallest cross-section of at least 1.0 cm$^2$, such at least 1.5 cm$^2$, preferably at least 2.0 cm$^2$.

Item 36. The breathing device (1) according to any of the preceding items, wherein the first wall section (3, 10, 16) or the month piece (2) has an average pore and/or through going opening size between about 2 nanometers and 2 millimeters or preferably above 2 mm.

Item 37. The breathing device (1) according to any of the preceding items, wherein the pores and/or through going openings are made by laser perforation.

Item 38. The breathing device (1) according to any of the preceding items, wherein the first wall section has a gas permeation flux for standard air determined at 20° C. and standard atmosphere (101.325 kPa), wherein the gas permeation flux is at least about 0.0005 m3/(sek*m2*kPa) and a pressure difference between the interior of the rebreathing air chamber and the surrounding atmosphere being between 5 and 35 Pascal.

Item 39. The breathing device (1) according to any of the preceding items, wherein the first wall section (3, 10, 16) comprises a polymer membrane, the polymer membrane preferably comprising polytetrafluoroethylene (PTFE), perfluoroalkoxy (PFA), fluorinated ethylene propylene (FEP), polyvinylidene difluoride (PVDF), polyethylene (PE), polypropylene (PP), paper, vegetable fibres, bio-degradable and/or combinations comprising any of the above mentioned polymers.

Item 40. The breathing device (1) according to any of the preceding items, wherein at least part of the rebreathing air chamber (15) is non-collapsible, preferably at least a part of rebreathing air chamber (15) is non-collapsible and a part of the rebreathing air chamber (15) is collapsible, more preferably the rebreathing air chamber (15) is partly collapsible and at least a sub-compartment closer to the breathing opening (5) into the rebreathing air chamber (15) is not collapsible or at least less collapsible than a sub-compartment farther from the breathing opening (5).

Item 41. The breathing device (1) according to any of the preceding items where one or more of the at least one through going opening is provided with a valve (38), preferably an adjustable valve for regulating the gas flow through the aperture, the adjustable valve preferably being automatically adjusted.

Item 42. The breathing device (1) according to any of the preceding items, wherein the rebreathing chamber (15) comprises a valve for draining off condensed water.

Item 43. The breathing device (1) according to any of the preceding items, wherein the breathing device comprises a $CO_2$ or $O_2$ sensing device incorporated into the breathing device, configured to measure the $CO_2$ and/or $O_2$ level of the inhaled and/or expired air.

Item 44. The breathing device (1) according to any of the preceding items, wherein the breathing device comprises a $O_2$ sensing device, is configured for measuring the $O_2$ level of the users blood.

Item 45. The breathing device (1) according to any of the preceding items, wherein the breathing device comprises at least one moisture absorbing element configured to absorb moisture from the rebreathing air chamber (15), the moisture absorbing element(s) preferably being at least partly placed in the rebreathing air chamber (15), more preferably the moisture absorbing element being a removable and replaceable element.

Item 46. The breathing device (1) according to any of the preceding items, wherein the breathing device comprises a flavouring device, such as flavouring to have the flavour of menthol, configured to change the odour of the rebreathing gas.

Item 47. The breathing device (1) according to any of the preceding items, wherein the second wall section (4) and/or first wall section (3) comprises a water transporting element configured to drain off water from the rebreathing air chamber (15), the water transporting element is made from or comprises a material which provides a path for transporting water from the rebreathing air chamber (15) to the surrounding atmosphere or to a water collecting unit.

Item 48. The breathing device (1) according to anyone of the preceding items, further comprising a cabinet (9, 21, 22) inside which a part of the mouth piece (2) and the rebreathing air chamber (15) is stored when not in use.

Item 49. The breathing device (1) according to item 48, wherein said part of the mouthpiece (2) and the rebreathing air chamber (15) is/are replaceable such as repositionally arranged in the cabinet.

Item 50. The breathing device (1) according to items 48 or 49, wherein the cabinet (21) comprises two detachable cabinet elements (22), such as lids, each replaceable such as repositionally arranged to an end of said cabinet (21), said two detachable cabinet elements preventing access to either said rebreathing air chamber (15) or breathing channel when device is not in use, said detachable cabinet elements (22) configured to provide access to said rebreathing air chamber (15) and/or to said breathing channel (2) when detached or replaced, such as repositioned.

Item 51. The breathing device (1) according to items 47-49, wherein said cabinet elements (22) are configured for being replaced, such as repositioned on two sides (23) adjacent to the ends where there is access to either said rebreathing air chamber (15) or breathing channel during non-use, so as to provide a better grip on the breathing device in use.

Item 52. A breathing device, according to any of the preceding items, in which the rebreathing air chamber (15) is detachable from, and re-attachable to, the mouth piece (2).

Item 53. A breathing device, according to any of the preceding items, further comprising a stability chamber/structure (13) attached, preferably not in direct fluid connection, to the rebreathing air chamber (15), configured to prevent complete collapse of the rebreathing air chamber during the inhalation phase of the rebreathing.

Item 54. A breathing device, according to any of the preceding items, wherein the rebreathing air chamber (15) comprises one or more deflation valves (14) configured to empty the rebreathing air chamber of air.

Item 55. A breathing device, according to any of the preceding items, for use in the treatment of migraine.

Item 56. A breathing device, according to any of the preceding items, for use in the treatment of epilepsy.

Item 57. A breathing device, according to any of the preceding items, for use in the treatment of febrile seizures.

Item 58. A breathing device, according to any of the preceding items, for use in the treatment of post-spinal headache.

Item 59. A breathing device, according to any of the preceding items, for use in the preventive treatment of asthma.

Item 60. A breathing device, according to any of the preceding items, for use in the treatment of Cardiac arrest.

Item 61. A breathing device according to any of the preceding items, wherein the rebreathing air chamber is foldable to reduce its size.

Item 62. A breathing device according to any of the items 7-61, wherein the rebreathing air-chamber-connecter (26), is foldable by comprising a number of parallel extending folding lines (32) arranged in said connector (26) to allow the air-breathing connector (26) to be folded into a configuration defining a void (33), preferably being cuboid, preferably the dimension of the breathing air-chamber connector (26) being selected so that when in folded configuration, at least part of the rebreathing air-chamber (15) is accommodated inside the void (33).

Item 63. A breathing device according to item 62, wherein the rebreathing air-chamber-connector (26) comprising a slider (24) providing an opening into said breathing air chamber (15) when said slider (24) is moved to one side, said slider (24) being configured for adjusting the flow of air into said rebreathing air chamber (15) by uncover or cover one or more through going opening (30).

Item 64. A breathing device according to any of the preceding items 62-63, wherein the rebreathing air-chamber-connector (26) comprising or further comprising through one or more through going openings (27), preferably being non-adjustable in size, and allowing fluid communication in and/or out of the rebreathing air chamber with the surrounding atmosphere.

Item 65. A breathing device according to any of the preceding items, 62-64, wherein the rebreathing air-chamber connector (26) comprising an elongate unfold element (34) extending slide-able in a direction being preferably being perpendicular to the folding lines along a surface of said connector (26) and being fixed at one end (34*a*) to said connector (26) so as to be configured for unfolding the rebreathing air-chamber-connector from its folded configuration by a user pulling in the elongate unfold element (34) at an end being opposite to the end being fixed.

Item 66. A breathing device according to item 65, wherein the rebreathing air-chamber connector (26) comprising guide elements (35) maintaining the elongate unfold element (34) in a guided position on said connector (2G).

Item 67. A breathing device according to item 65 or 66, wherein the elongate unfold element (34) and/or the rebreathing air-chamber connector (26) comprising a latch configured for latching the elongate unfold element's position when the said rebreathing air-chamber connector (26) is in its unfolded configuration.

Item 68. A breathing device, according to any of the preceding items, wherein the rebreathing air-chamber (15) comprises a strip (37) attached to a wall section of the rebreathing air-chamber allowing a user to expand the rebreathing air-chamber (15), preferably to unfold the rebreathing air-chamber from a folded configured, so as to make it easier for a user to exhale air into the rebreathing air-chamber.

General Remarks

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

LIST OF REFERENCE SYMBOLS USED

1 Breathing device
2 Mouthpiece/breathing channel
3 First wall section
4 Second wall section
5 Breathing opening
6 Flow opening
7 Flow opening
8 Flow opening
9 Cabinet
10 Hole-perforated wall material, preferably be flexible
11 Flexible wall section perforated with row(s) of holes
12 Non-return valve for inflating structural support chamber 13
13 Structural stability chamber
14 Deflation valve
15 Rebreathing air chamber
16 Flexible first wall
17 Cube
18 Flexible second wall
19 Through going opening
20 Wall section
21 Cabinet
22 Cabinet element
23 Adjacent side
24 Slider
25 Wall section
26 Rebreathing air-chamber-connector
27 Non-adjustable trough going openings
28 Part of connector with trough goings openings
29 Socket
30 Through going opening
31 Hinge
32 Folding line
33 Void, preferably being open at a proximal and distal end
34 Unfold element
34a Fixed position of elongate fold element 34
35 Guide elements
36 Pore(s)
37 Strip, such as a pull-tab
38 Mechanical valve

The invention claimed is:

1. A breathing device, comprising:
a mouthpiece forming a breathing channel to form a connection between a first end and a second end of the mouthpiece, the first end being configured for a user breathing into the mouthpiece through a breathing opening,
an at least partly flexible rebreathing air chamber attached to the second end of the mouthpiece, thereby being in fluid connection with the breathing channel, the rebreathing air chamber being formed by an at least partly flexible wall section(s), wherein—the at least partly flexible rebreathing chamber having a first wall section being permeable to gas by a plurality of through going openings provided in a rebreathing-air-chamber connector, wherein one or more of said through going openings are re-closable and/or adjustable openings.

2. A breathing device according to claim 1, wherein
said first wall section being at least partly flexible, said through going openings provide a permeability to gas and having an overall flow conductance G, and
wherein the first wall section apart from said through going openings is non-permeable togas and deformable by a pressure differences across said first wall section, wherein said pressure difference is of a size provided by a user breathing into the rebreathing air chamber, giving the rebreathing chamber enclosed by said first wall section a substantial time-normalized compliance C, where C is determined as the volume expansion of the rebreathing chamber per second per pressure difference across said wall section, wherein said rebreathing air chamber has a Rebreathing Ratio, as defined herein, between 0.5 and 0.95.

3. A breathing device according to claim 1, wherein said rebreathing air chamber comprises
said first wall section being permeable to gas and having a first conductance $G_{out}$ and
a second wall section being impermeable togas and having a second conductance $G_{expand}$ wherein the first and the second wall section are configured to provide an RBR defined as RBR=$G_{expand}/(G_{out}+G_{expand})$ between 0.5 and 0.9.

4. A breathing device according to claim 1, wherein the rebreathing air chamber comprising the first wall section being permeable to air and a second wall section being impermeable to air.

5. A breathing device according to claim 1, wherein said rebreathing air chamber being formed by the first wall section wherein the first wall section being flexible.

6. A breathing device according to claim 1, wherein the rebreathing air-chamber-connector being configured
for connecting a facial mask or said mouthpiece to said rebreathing air chamber; and at least a part of said rebreathing-air-chamber-connector forming at least part of the first wall section and/or a second wall section, said rebreathing-air-chamber-connector allowing fluid communication in and/or out of the re-breathing air chamber with a user's breath.

7. A breathing device according to claim 1, wherein the form of said rebreathing air chamber is selected from the group consisting of: cube, cuboid, sphere, spheroid, bag type, tetrahedron, substantially tetrahedron, square-based pyramid substantially pyramid, octahedron, substantially octahedron, hexagonal prism substantially prism, dodecahedron, substantially dodecahedron, cylinder, or cylindroid.

8. A breathing device according to claim 7, wherein the rebreathing air chamber comprising panels each defining a face of the rebreathing air chamber, one or more of said panels and/or at least a part of one of said panels forms said first wall section, at least one of said panels form at least a part of a second flexible wall section, said first wall section comprising permeable sections or being permeable togas by the plurality through going openings preferably arranged in lines or rows, distributed in the first wall section.

9. A breathing device according to claim 8, wherein one or more of said panels comprise the first wall section being flexible and/or second wall section.

10. A breathing device according to claim 8, wherein said panels and/or wall sections has a thickness smaller than 4 mm.

11. A breathing device according to claim 6, wherein said rebreathing air chamber further comprises said breathing channel arranged in said rebreathing-air-chamber-connector, allowing fluid communication in and/or out of the rebreathing air chamber with the user's mouth, during use.

12. A breathing device according to claim 6, wherein said breathing channel has at least one through going opening, allowing fluid communication in and/or out of the breathing device with the surrounding atmosphere.

13. A breathing device according to claim 12, wherein one or more of said at least one through going openings are re-closable and/or adjustable in size by a valve mechanism.

14. A breathing device according to claim 12, wherein said at least one through going opening provided in the breathing channel are in the form of one or more opening covered by a slider, arranged between two parallel longitudinal wall sections, said slider providing an opening into said breathing channel when said slider is moved translatory between the two parallel longitudinal wall sections, said slider configured for adjusting the flow of air into said rebreathing air chamber.

15. A breathing device according to claim 12, wherein said breathing channel further comprises two parallel longitudinal wall sections, protruding in a perpendicular direction to a breathing direction through the breathing channel, with a distance in between measured as the distance between the two parallel longitudinal wall sections below 3 cm, configured for the user being preventing from blocking the through going openings with a finger, while holding said breathing device with the fingers, said through going openings being arranged in between the two parallel longitudinal wall sections.

16. A breathing device according to claim 6, wherein the rebreathing air chamber comprises non-adjustable through going openings, arranged on the rebreathing-air-chamber-connector allowing fluid communication in and/or out of the rebreathing air chamber with the surrounding atmosphere.

17. A breathing device according to claim 6, wherein said rebreathing air chamber-connector further comprises a socket configured for connecting the rebreathing air chamber to the mouthpiece while allowing fluid communication in and/or out of the rebreathing air chamber.

18. A breathing device according to claim 17, further comprising: wherein one or more of the re-closable and/or adjustable openings comprises a slider arranged between two parallel longitudinal wall sections, said slider arranged on said wall section, said slider providing an opening into said breathing air chamber when said slider is moved to one side between the two parallel longitudinal wall sections, said slider being configured for adjusting the flow of air into said rebreathing air chamber.

19. A breathing device according to claim 17, wherein the socket forms the mouth piece.

20. A breathing device according to claim 1, wherein the first wall section of the at least partly flexible rebreathing chamber being permeable to gas by one or more pores provided in said wall section.

21. A breathing device, comprising:
a mouthpiece forming a breathing channel to form a connection between a first end and a second end of the mouthpiece, the first end being configured for a user breathing into the mouthpiece through a breathing opening,
an at least partly flexible rebreathing air chamber attached to the second end of the mouthpiece, thereby being in fluid connection with the breathing channel, the rebreathing air chamber being formed by an at least partly wall section(s),
wherein
the at least partly flexible rebreathing chamber having a first wall section being permeable to gas by a plurality of through going openings provided in a rebreathing-air-chamber connector wherein one or more of said through going openings are re-closable and/or adjustable openings, and
the mouthpiece comprising one or more through going openings allowing fluid communication between the breathing channel and the surrounding atmosphere wherein one or more of said through going openings are re-closable and/or adjustable in size.

* * * * *